US011857361B2

(12) United States Patent
Hakkens et al.

(10) Patent No.: US 11,857,361 B2
(45) Date of Patent: Jan. 2, 2024

(54) ACOUSTICALLY TRANSPARENT WINDOW FOR INTRALUMINAL ULTRASOUND IMAGING DEVICE

(71) Applicant: KONINKLIJKE PHILIPS N.V., Eindhoven (NL)

(72) Inventors: Franciscus Johannes Gerardus Hakkens, Eersel (NL); Lucas Johannes Anna Maria Beckers, Veldhoven (NL); Johannes Wilhelmus Weekamp, Beek en Donk (NL); Peter Dirksen, Hilversum (NL); Petrus Henricus Maria Timmermans, Teteringen (NL); Sergei Y. Shulepov, Eindhoven (NL); Hans-Peter Loebl, Monschau-Imgenbroich (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 45 days.

(21) Appl. No.: 17/256,248

(22) PCT Filed: Jun. 28, 2019

(86) PCT No.: PCT/EP2019/067499
§ 371 (c)(1),
(2) Date: Dec. 28, 2020

(87) PCT Pub. No.: WO2020/007753
PCT Pub. Date: Jan. 9, 2020

(65) Prior Publication Data
US 2021/0128107 A1 May 6, 2021

(30) Foreign Application Priority Data
Jul. 2, 2018 (EP) .................................. 18181154

(51) Int. Cl.
*A61B 8/12* (2006.01)
*A61B 8/00* (2006.01)
(Continued)

(52) U.S. Cl.
CPC ................ *A61B 8/12* (2013.01); *A61B 8/445* (2013.01); *A61B 8/4477* (2013.01);
(Continued)

(58) Field of Classification Search
CPC ......... A61B 8/12; A61B 8/445; A61B 8/4483; G01S 15/8906; B06B 1/0292; H10N 30/2047; G01N 29/2406
See application file for complete search history.

(56) References Cited

U.S. PATENT DOCUMENTS 6,689,066 B1 2/2004 Omura
6,776,763 B2 8/2004 Nix
(Continued)

FOREIGN PATENT DOCUMENTS

JP 592312 U 1/1994
JP H07323031 A 12/1995
(Continued)

OTHER PUBLICATIONS

K. Kirk Shung, Diagnostic Ultrasound: Imaging and Blood Flow Measurements, 2015, CRC Press, Second Edition, pp. 57-58 (Year: 2015).*
(Continued)

*Primary Examiner* — Colin T. Sakamoto
*Assistant Examiner* — Tommy T Ly

(57) ABSTRACT

An intraluminal ultrasound imaging device includes a flexible elongate member configured to be positioned within a body lumen of a patient. An ultrasound imaging assembly is disposed at the distal portion of the flexible elongate member. The ultrasound imaging assembly includes a plurality of
(Continued)

acoustic elements and an acoustically-transparent window disposed over the plurality of acoustic elements. The acoustically-transparent window comprising a plurality of layers formed on top of one another. The plurality of layers includes an innermost layer directly contacting the plurality of acoustic elements, an outermost layer opposite the innermost layer, and an adhesive layer. The outermost layer includes a tubing. A hardness of the innermost layer is less than hardnesses of every other layer of the plurality of layers. A hardness of the outermost layer is greater than the hardnesses of every other layer of the plurality of layers.

26 Claims, 14 Drawing Sheets

(51) Int. Cl.
  G01S 7/52 (2006.01)
  G01S 15/89 (2006.01)
(52) U.S. Cl.
  CPC ........ A61B 8/4494 (2013.01); G01S 7/52085 (2013.01); G01S 15/8906 (2013.01)

(56) References Cited

U.S. PATENT DOCUMENTS

| | | | |
|---|---|---|---|
| 7,226,417 B1 | 6/2007 | Eberle | |
| 7,846,101 B2 | 12/2010 | Eberle | |
| 2005/0228286 A1* | 10/2005 | Messerly | A61B 8/445 600/459 |
| 2013/0301394 A1* | 11/2013 | Chen | A61B 8/4272 367/157 |
| 2014/0184023 A1 | 7/2014 | Rice | |
| 2014/0187964 A1 | 7/2014 | Corl | |
| 2016/0081657 A1* | 3/2016 | Rice | A61B 8/445 600/467 |
| 2016/0101437 A1 | 4/2016 | Chen | |
| 2016/0325024 A1 | 11/2016 | Lin | |

FOREIGN PATENT DOCUMENTS

| | | | | |
|---|---|---|---|---|
| JP | 2003299195 A | | 10/2003 | |
| WO | WO-2016091985 A1 | * | 6/2016 | ............... A61B 8/12 |
| WO | 2016139103 A1 | | 9/2016 | |
| WO | WO-2016139103 A1 | * | 9/2016 | ............... B06B 1/02 |
| WO | WO-2017025438 A1 | * | 2/2017 | ........... A61B 8/4483 |
| WO | WO-2017081138 A1 | * | 5/2017 | ........... A61B 8/4483 |
| WO | 2017103172 A1 | | 6/2017 | |
| WO | WO-2018041658 A2 | * | 3/2018 | ............... A61B 8/12 |
| WO | 2019002231 A1 | | 1/2019 | |
| WO | 2019110334 A1 | | 6/2019 | |
| WO | 2019110698 A1 | | 6/2019 | |
| WO | 2019110776 A1 | | 6/2019 | |

OTHER PUBLICATIONS

International Search Report & Written Opinion of PCT/EP2019/067499, dated Oct. 2, 2019.

* cited by examiner

ACOUSTICALLY TRANSPARENT WINDOW FOR INTRALUMINAL ULTRASOUND IMAGING DEVICE

CROSS-REFERENCE TO PRIOR APPLICATIONS

This application is the U.S. National Phase application under 35 U.S.C. § 371 of International Application No. PCT/EP2019/067499, filed on Jun. 28, 2019, which claims the benefit of European Patent Application No. 18181154.8, filed on Jul. 2, 2018. These applications are hereby incorporated by reference herein.

TECHNICAL FIELD

The present disclosure relates generally to an acoustically-transparent window through which ultrasound energy associated with an ultrasound transducer array propagates. The ultrasound transducer array can be part of an intraluminal ultrasound imaging device, such as an intravascular ultrasound (IVUS) imaging catheter. In an exemplary embodiment, the acoustic window includes multiple layers, including an outermost shrink wrap layer that has the largest hardness of all the layers and a flexible, innermost layer that has the smallest hardness of all the layers

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducer elements is passed into the vessel and guided to the area to be imaged. The transducer elements emit ultrasonic energy in the form of ultrasonic waves in order to create an image of the vessel of interest. The ultrasonic waves are partially reflected by discontinuities arising from tissue structures (such as the various layers of the vessel wall), red blood cells, and other features of interest. The reflected waves are received by the transducer elements and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducer elements distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Imaging elements in existing IVUS catheters are typically formed from a ceramic material that has piezoelectric properties, such as lead zirconate titanate (PZT). Many external (on body) ultrasound transducers also utilize PZT elements. Acoustic windows utilized for PZT transducers are formed of a relatively hard material that is rigid and not conformable. For example, external transducers utilize ceramic particle filled silicones. Intravascular applications like IVUS utilize thinner but still hard windows formed of polyimide. Efforts have been made to deploy capacitive micromachined ultrasound transducer (CMUT) elements, instead of PZT elements, for ultrasound imaging. These efforts have been hindered by the lack of a suitable acoustic window.

SUMMARY

The present application describes an intraluminal ultrasound imaging device with an acoustic window structure that can be utilized with capacitive micromachined ultrasound transducer (CMUT) elements. The intraluminal ultrasound imaging device, such as a catheter or a guide wire, includes an array of CMUT elements, and the acoustic window is positioned over the CMUT elements. The acoustic window includes multiple layers, including an innermost layer that is in direct contact with the CMUT elements. The innermost layer is formed of an elastic material that has the least hardness of the all of the layers in the acoustic window. Thus, the innermost layer is deformable when the membrane of the CMUT element moves when emitting and receiving ultrasound energy. The outermost layer has the most hardness of all of the layers in the acoustic window. Thus, the acoustic window protects the CMUT elements during exposure to anatomy within the patient body (e.g., calcified stenosis in a blood vessel). The outermost layer can be a shrink wrap tubing in some instances, which advantageously allows for efficient manufacturing of the imaging catheter or guide wire.

According to an exemplary embodiment, intraluminal ultrasound imaging device is provided. The device includes a flexible elongate member configured to be positioned within a body lumen of a patient, the flexible elongate member comprising a proximal portion, a distal portion, and a longitudinal axis; an ultrasound imaging assembly disposed at the distal portion of the flexible elongate member and configured to obtain imaging data while positioned within the body lumen, the ultrasound imaging assembly comprising: a plurality of acoustic elements arranged around the longitudinal axis of the flexible elongate member; and an acoustically-transparent window disposed over the plurality of acoustic elements, the acoustically-transparent window comprising a plurality of layers formed on top of one another, wherein the plurality of layers comprises: an innermost layer directly contacting the plurality of acoustic elements; an outermost layer opposite the innermost layer, wherein the outermost layer comprises a tubing; and an adhesive layer coupling the outermost layer to another layer of the plurality of layers, wherein a hardness of the innermost layer is less than hardnesses of every other layer of the plurality of layers, and wherein a hardness of the outermost layer is greater than the hardnesses of every other layer of the plurality of layers.

In some embodiments, the flexible elongate member comprises a catheter. In some embodiments, the ultrasound imaging assembly comprises an intravascular ultrasound (IVUS) imaging assembly. In some embodiments, the plurality of acoustic elements comprises capacitive micromachined ultrasound transducer (CMUT) elements. In some embodiments, the tubing comprising a shrink wrap tubing. In some embodiments, each of the plurality of acoustic elements comprises a substrate and a membrane movable relative to the substrate, and the innermost layer comprises an elastic material deformable upon movement of the membrane. In some embodiments, the innermost layer comprises polybutadiene rubber (PBR). In some embodiments, the outermost layer comprises polyethylene terephthalate (PET). In some embodiments, the adhesive layer comprises polyurethane (PU).

According to an exemplary embodiment, an intraluminal ultrasound imaging system is provided. The system includes an ultrasound imaging catheter configured to obtain imaging data while positioned within a body lumen of a patient, the ultrasound imaging catheter comprising a proximal portion, a distal portion, and a longitudinal axis, wherein the ultrasound imaging catheter further comprises: a plurality of acoustic elements disposed at the distal portion and arranged around the longitudinal axis; and an acoustically-transparent window disposed over the plurality of acoustic elements, the acoustically-transparent window comprising: a first material layer positioned over and directly contacting the plurality of acoustic elements, the first material layer comprising a first hardness; a second material layer positioned over and directly contacting the first material layer, the second material layer comprising a second hardness; and a third material layer positioned over and directly contacting the second material layer, the third material layer comprising a tubing having a third hardness, wherein the second material layer couples the first material layer and the third material layer, wherein the first hardness is less than the second hardness and the third hardness, and wherein the third hardness is greater than the first hardness and the second hardness; and a processor in communication with the ultrasound imaging catheter and configured to output, to a display, an ultrasound image based on the obtained imaging data.

In some embodiments, the ultrasound imaging catheter comprises an intravascular ultrasound (IVUS) catheter. In some embodiments, the plurality of acoustic elements comprises capacitive micromachined ultrasound transducer (CMUT) elements. In some embodiments, the tubing comprising a shrink wrap tubing. In some embodiments, each of the plurality of acoustic elements comprises a substrate and a membrane movable relative to the substrate, and the first material layer comprises an elastic material deformable upon movement of the membrane. In some embodiments, the first material layer comprises polybutadiene rubber (PBR). In some embodiments, the third material layer comprises polyethylene terephthalate (PET). In some embodiments, the second material layer comprises polyurethane (PU).

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 12 is a diagrammatic top view of an acoustic element array, according to an embodiment of the present disclosure.

FIG. 13 is a diagrammatic top view after a flexible layer of an acoustically-transparent window has been distributed over the acoustic element array and cured, according to an embodiment of the present disclosure.

FIG. 14 is a diagrammatic top view of a heat shrink tubing arranged to be positioned over the acoustic element array including an adhesive dispensed on the flexible layer of the acoustically-transparent window, according to an embodiment of the present disclosure.

FIG. 15 is a diagrammatic top view after shrinking the tubing and curing the adhesive to form the acoustically-transparent window, according to an embodiment of the present disclosure.

FIG. 16 shows a process of deposition of material for a lowermost layer of the acoustically-transparent window for forming a window having a thickness which varies across its extent.

FIG. 17 is a diagrammatic top view of CMUT elements visible through the acoustically-transparent window, according to an embodiment of the present disclosure.

DETAILED DESCRIPTION

Figure 1:
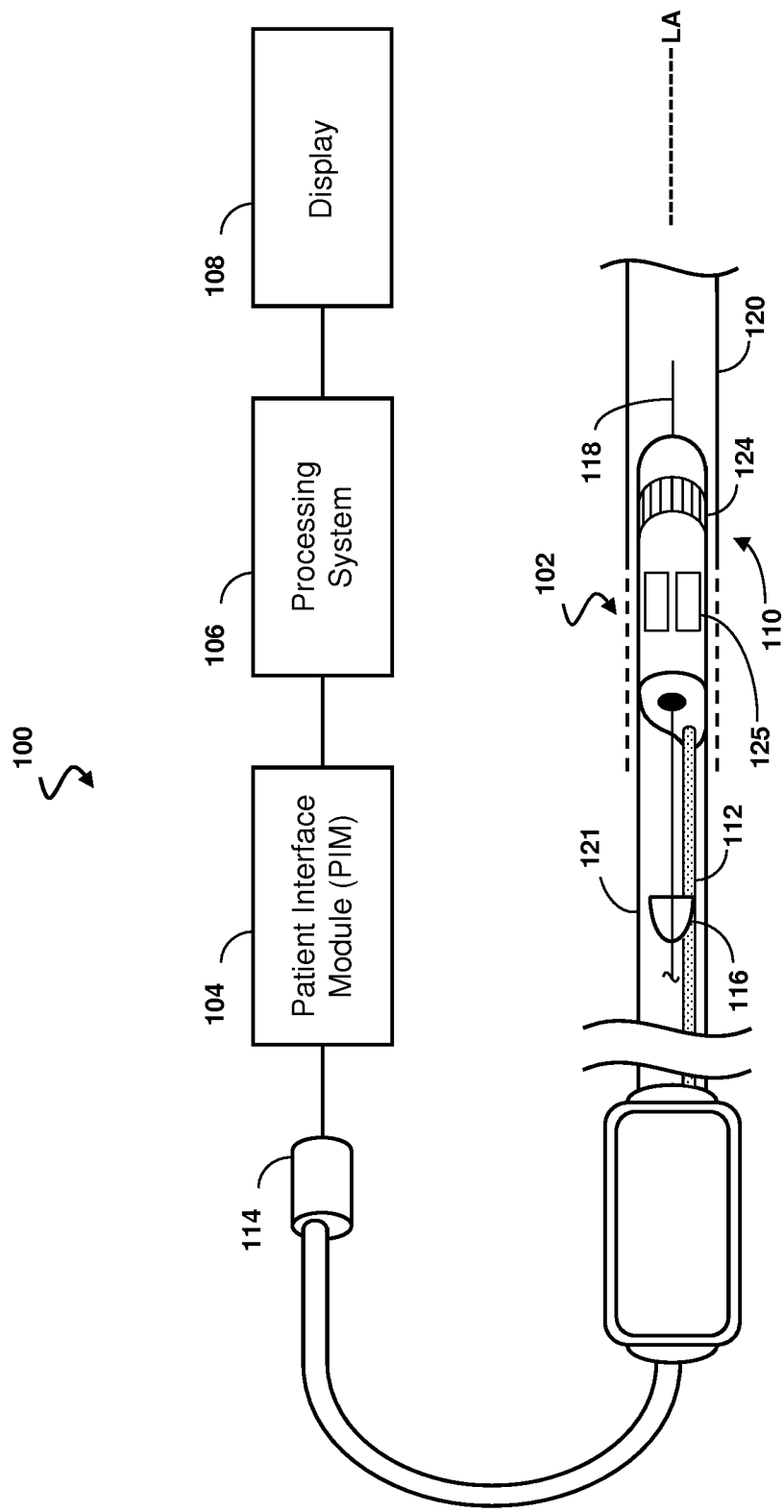
FIG. 1 is a diagrammatic schematic view of an intraluminal ultrasound imaging system, according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while aspects of the present disclosure are described in terms of intraluminal ultrasound imaging, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intraluminal ultrasound imaging system 100, according to aspects of the present disclosure. For example, the system 100 can be intravascular ultrasound (IVUS) imaging system. The intraluminal ultrasound imaging system 100 includes an intraluminal ultrasound imaging device 102, a patient interface module (PIM) 104, a processing system 106, and a display 108. The intraluminal ultrasound imaging device 102 can be an IVUS imaging device, such as a catheter, guide wire, or guide catheter.

At a high level, the IVUS device 102 emits ultrasonic energy from a transducer or acoustic element array 124 included in the ultrasound imaging or scanner assembly 110 mounted near a distal end of the catheter or flexible elongate member 121. The flexible elongate member 121 can be referenced as a longitudinal body in some instances. The flexible elongate member 121 can include a proximal portion and a distal portion opposite the proximal portion. The array 124 can be positioned around a longitudinal axis LA of the imaging assembly 110 and/or the flexible elongate member 121. The ultrasonic energy is reflected by tissue structures in the medium, such as a body lumen 120, surrounding the scanner assembly 110, and the ultrasound echo signals are received by the transducer array 124. The PIM 104 transfers the received echo signals to the processing system 106 where the ultrasound image (including B-mode and/or flow data) is reconstructed and displayed on the display 108. The display 108 can be referenced as a monitor in some instances. The processing system 106 can include a processor and a memory. The processing system 106 can be referenced as a console, computer, and/or computing system in some instances. The processing system 106 can be operable to facilitate the features of the IVUS imaging system 100 described herein. For example, the processor can execute computer readable instructions stored on the non-transitory tangible computer readable medium The scanner assembly 110 may include one or more controllers 125, such as control logic integrated circuits (IC), in communication with the array 124. For example, the controllers 125 can be application specific integrated circuits (ASICs). The controllers 125 can be in communication with the array 124 via conductors, such as conductive traces in or on a substrate. The controllers 125 are configured to control operations of the array 124 associated with emitting and/or receiving ultrasound energy to obtain imaging data associated with the body lumen 120. The scanner assembly 110 can include any suitable number of controllers 125, including one, two, three, four, five, six, seven, eight, nine, or more controllers. In some embodiments, the controllers 125 (FIG. 1) can be mounted on the imaging assembly 110 longitudinally proximal to the transducer array 124. In some other embodiments, the one or more control logic ICs can be disposed between the rolled-around transducer array 124 and the tubular member 126. The controllers 125 can be referenced as control logic circuitry, chips, or integrated circuits (ICs) in some instances. Aspects of an intraluminal imaging device, including various techniques of transforming the transducer array 124 from a flat configuration to a cylindrical or rolled-around configuration, are disclosed in one or more of U.S. Pat. Nos. 6,776,763, 7,226,417, U.S. Provisional App. No. 62/596,154, filed Dec. 8, 2017, U.S. Provisional App. No. 62/596,141, filed Dec. 8, 2017, U.S. Provisional App. No. 62/596,300, filed Dec. 8, 2017, U.S. Provisional App. No. 62/596,205, filed Dec. 8, 2017, each of which is hereby incorporated by reference in its entirety.

In some embodiments, the acoustic elements of the array 124 and/or the controllers 125 can be positioned in an annular configuration, such as a circular configuration or in a polygon configuration, around the longitudinal axis LA. It will be understood that the longitudinal axis LA of the support member 126 may also be referred to as the longitudinal axis of the scanner assembly 110, the flexible elongate member 115, the device 102, and/or the support member 126 of FIG. 2. For example, a cross-sectional profile of the imaging assembly 110 at the transducer elements of the array 124 and/or the controllers 125 can be a circle or a polygon. Any suitable annular polygon shape can be implemented, such as a based on the number of controllers/transducers, flexibility of the controllers/transducers, etc., including a pentagon, hexagon, heptagon, octagon, nonagon, decagon, etc.

The PIM 104 facilitates communication of signals between the processing system 106, such as an IVUS console, and the scanner assembly 110 included in the IVUS device 102. This communication includes the steps of: (1) providing commands to one or more control logic integrated circuits included in the scanner assembly 110 to select the particular transducer array element(s) to be used for transmit and receive, (2) providing the transmit trigger signals to the one or more control logic integrated circuits included in the scanner assembly 110 to activate the transmitter circuitry to generate an electrical pulse to excite the selected transducer array element(s), and/or (3) accepting amplified echo signals received from the selected transducer array element(s) via amplifiers included on the one or more control logic integrated circuits of the scanner assembly 110. In some embodiments, the PIM 104 performs preliminary processing of the echo data prior to relaying the data to the processing system 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The processing system 106 receives the echo data from the scanner assembly 110 by way of the PIM 104 and processes the data to reconstruct an image of the tissue structures in the medium surrounding the ultrasound imaging assembly 110. The processing system 106 outputs image data such that an image of the body lumen 120, such as a cross-sectional image of a vessel, is displayed on the display 108. Generally, the system 100 and/or the device 102 can be used in any suitable lumen of a patient body. In that regard, the system 100 can be an intraluminal ultrasound imaging system, and the device 102 can be an intraluminal ultrasound imaging device. In some instances, the device 102 can be an intra-cardiac echocardiography (ICE) imaging catheter or a trans-esophageal echocardiography (TEE) probe. The system 100 and/or the device 102 can be referenced as an interventional device, a therapeutic device, a diagnostic device, etc. The device 102 can be sized and shaped, structurally arranged, and/or otherwise configured to be positioned within the body lumen 120. Body lumen 120 may represent fluid filled or surrounded structures, both natural and man-made. The body lumen 120 may be within a body of a patient. The body lumen 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

In some embodiments, the IVUS device includes some features similar to traditional solid-state IVUS catheters, such as the EagleEye® catheter available from Koninklijke Philips N.V. and those disclosed in U.S. Pat. No. 7,846,101 hereby incorporated by reference in its entirety. For example, the IVUS device 102 includes the scanner assembly 110 near a distal end of the flexible elongate member 121 and a cable 112 extending along the flexible elongate member 121. The cable 112 can include a plurality of communication lines, including one, two, three, four, five, six, seven, or more communication lines 134 (as shown for example in FIG. 2). Any suitable communication lines 134 can be implemented, such as a conductors, fiber optics, etc. It is understood that any suitable gauge wire, for example, can be used for the communication lines 134. In an embodiment, the cable 112 can include a four-conductor transmission line arrangement with, e.g., 41 AWG gauge wires. The cable 112 can be referenced as a transmission-line bundle in some instances. In an embodiment, the cable 112 can include a seven-conductor transmission line arrangement utilizing, e.g., 44 AWG gauge wires. In some embodiments, 43 AWG gauge wires can be used.

The cable 112 terminates in a PIM connector 114 at a proximal end of the device 102. The PIM connector 114 electrically couples the cable 112 to the PIM 104 and physically couples the IVUS device 102 to the PIM 104. In an embodiment, the IVUS device 102 further includes a guide wire exit port 116. Accordingly, in some instances, the IVUS device 102 is a rapid-exchange catheter. The guide wire exit port 116 allows a guide wire 118 to be inserted towards the distal end in order to direct the device 102 through the body lumen 120. In other instances, the IVUS device 102 can be an over-the-wire catheter including a guide wire lumen extending along an entire length of the flexible elongate member 121. The flexible elongate member 121 can be made of polymeric lengths of tubing in some instances, including one or more lumens for the cable 112 and/or the guide wire 118.

Figure 2:
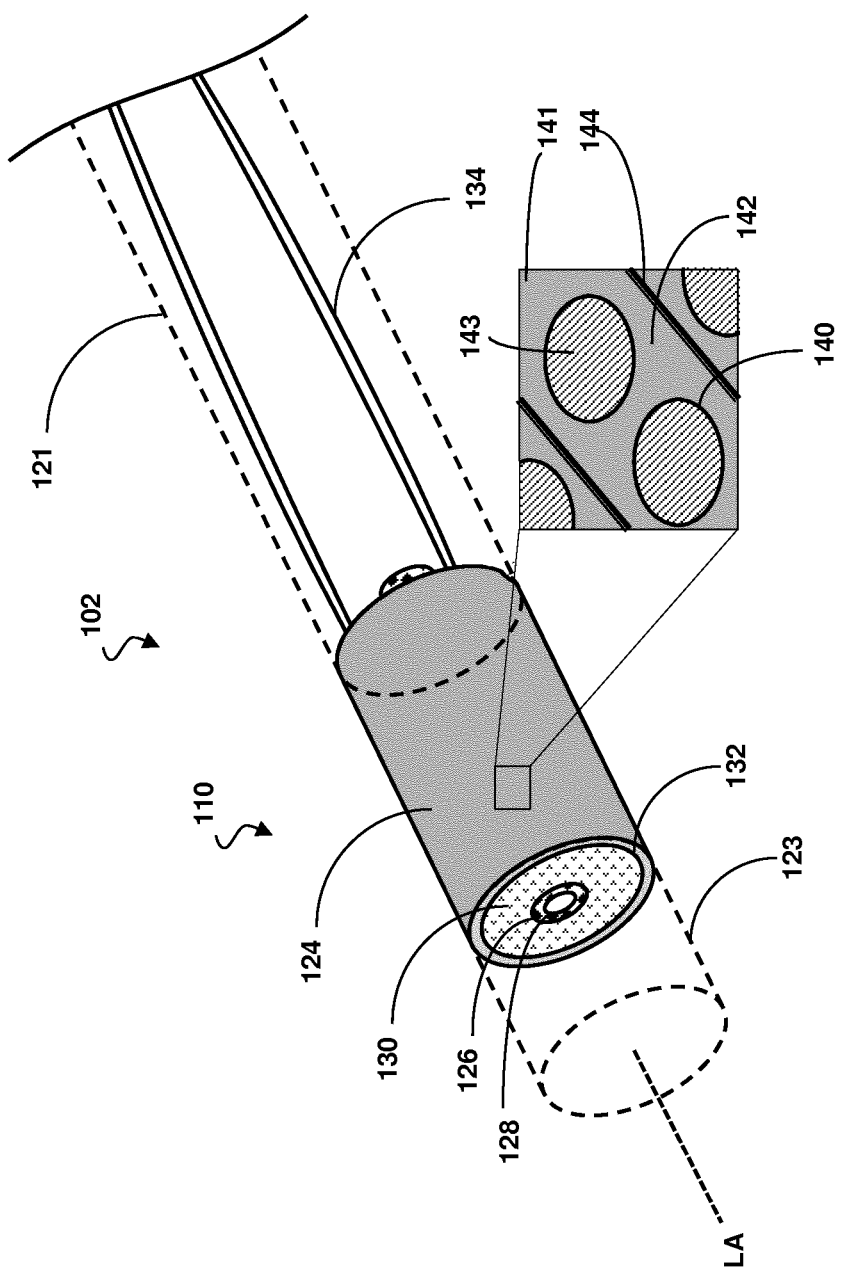
FIG. 2 is a diagrammatic perspective view of an intraluminal ultrasound imaging device including an ultrasound imaging assembly, according to an embodiment of the present disclosure.

FIG. 2 is a diagrammatic perspective view of the intraluminal imaging device 102, including the ultrasound scanner assembly 110. In some embodiments, the ultrasound scanner assembly 110 can be disposed at a distal portion of the flexible elongate member 121 of the device 102. The flexible elongate member 121 is sized and shaped, structurally arranged, and/or otherwise configured to be positioned within a body lumen of a patient. The imaging or scanner assembly 110 obtains ultrasound imaging data associated with the body lumen while the device 102 is positioned within the body lumen. As shown in FIG. 2, the scanner assembly 110 may include the transducer array 124 positioned around the longitudinal axis LA of the device 102. The transducer array 124 can be referenced as an array of acoustic elements in some instances. In some instances, the scanner assembly 110 can include a diameter between about 0.8 mm and about 1.6 mm, such as 1.2 mm.

The array 124 is disposed in a rolled or cylindrical configuration around a tubular member 126. The tubular member 126 can also be referred to as a support member, a unibody member, or a ferrule. In some implementations, the tubular member 126 can include a lumen 128. The lumen 128 can be sized and shaped to receive a guide wire, such as the guide wire 118 shown in FIG. 1. The device 102 can be configured to be moved along or ride on the guide wire 118 to a desired location within the physiology of the patient. In those implementations, the lumen 128 can be referred to as a guide wire lumen 128.

In some embodiments, the scanner assembly 110 may also include a backing material 130 between the transducer array 124 and the tubular member 126. In that regard, the tubular member 126 can include stands that radially space the transducer array 124 from the body of the support member 126. The backing material 130 can be disposed within the radial space between the tubular member 126 and the array 124. The backing material 130 serves as an acoustic damper to minimize or eliminate propagation of ultrasound energy in undesired directions (e.g., radially towards the center) Thus, the ultrasound energy from the array 124 is directed radially towards the body lumen 120 in which the flexible elongate member 121 is positioned.

Figure 9:
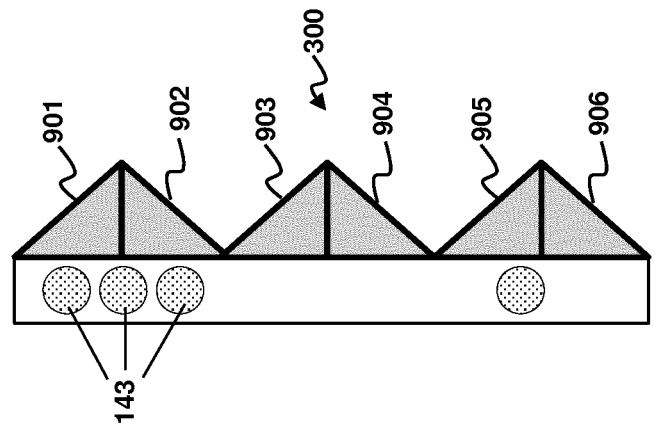
FIGS. 7-9 illustrate different example structural arrangements for acoustically transparent windows having thicknesses which vary.

As shown in the enlarged view of a region of the transducer array 124, the transducer array 124 can include a plurality of rows of acoustic/transducer elements 140 fabricated on a semiconductor substrate 132. The semiconductor substrate 132 is divided into a plurality of islands 141 spaced apart from one another and/or separated by trenches 144. The trenches 144 isolate the islands 141, which allows islands to be orientated at different angles, such as when the array 124 is positioned around the longitudinal axis LA of the device 102. The imaging assembly 110 can include any suitable number of islands 141, such as 4, 8, 16, 32, 64, 128, and/or other values both larger and smaller. A plurality of acoustic elements 140 can be formed on each island 141. In some instances, a single row of acoustic elements 140 can be formed on each island, as shown in FIG. 2. In other instances, two rows of acoustic elements 140 can be formed on each island and arranged in a staggered manner, as shown in FIG. 9. In some embodiments, the acoustic elements 140 can be positioned side-by-side one another on an individual island 141.

In some embodiments, the substrate 132 may be formed of a semiconductor material. Each of the ultrasound transducer elements 140 in the transducer array 124 can be a micromachined ultrasound transducer, such as a capacitive micromachined ultrasound transducer (CMUT) or a piezoelectric micromachined ultrasound transducer (PMUT). While each of the ultrasound transducer elements 140 is illustrated as being circular in shape, it should be understood that each of the ultrasound transducer elements 140 can be in any shape.

The divided islands 141 of the semiconductor substrate 132 are coupled to a common flexible interconnect 142. The flexible interconnect 142 can extend around the acoustic elements 140 as well as across and/or over the trenches 144. The flexible interconnect 142 can include holes aligned with a diaphragm or movable membrane 143 of the acoustic elements 140. In that regard, the interconnect 142 does not completely cover the islands 141. The interconnect 142 can cover portions of the islands 141 that do not include the diaphragm or movable membrane 143 of the acoustic elements 140. In some embodiments, the interconnect 142 completely covers the islands 141, including the diaphragm or movable membrane 143 of the acoustic elements 140, such as when the flexible interconnect 142 also comprises an acoustic matching layer. As described herein, an acoustically-transparent window can be disposed over the acoustic elements 140

The flexible interconnect 142 can be made of polymer material, such as polyimide (for example, KAPTON™ (trademark of DuPont)), and can be considered a flexible substrate. Other suitable polymer materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont) As the transducer array 124 is first fabricated on the semiconductor substrate 132, which is rigid, and then a flexible substrate (i.e. the flexible interconnect 142) is positioned over the transducer array 124, the transducer array 124 is fabricated using flexible-to-rigid (F2R) technology. The trenches 144 are positioned under the flexible interconnect 142 and form the fold lines when the transducer array 124 is rolled around the tubular member 126. That is, the array 124 can be manufactured in a flat configuration and transitioned into a cylindrical or rolled configuration around the longitudinal axis of the flexible elongate member 121 during assembly of the device 102. Exemplary aspects of manufacturing the ultrasound imaging assembly are described in U.S. Provisional App. No. 62/527,143, filed Jun. 30, 2017, and U.S. Provisional App. No. 62/679,134, filed Jun. 1, 2018, each of which is hereby incorporated by reference in its entirety. While flex-to-rigid (F2R) and/or the flexible interconnect 142 are mentioned, it is understood that acoustically-transparent window described herein can be implemented in other intraluminal device architectures, including intraluminal devices without F2R and/or the flexible interconnect 142.

A tip member 123 defines the distal end of the device 102. The tip member 123 is the leading component of the device 102 as the device 102 is inserted into and moved within the body lumen 120. The tip member 123 can be formed of a polymer material such that the device 102 atraumatically contacts anatomy. The tip member 123 can include a guide wire lumen in communication with the lumen 128 of the support member 126 such that the guide wire 118 extends through the support member 126 and the tip member 123.

Figure 3:
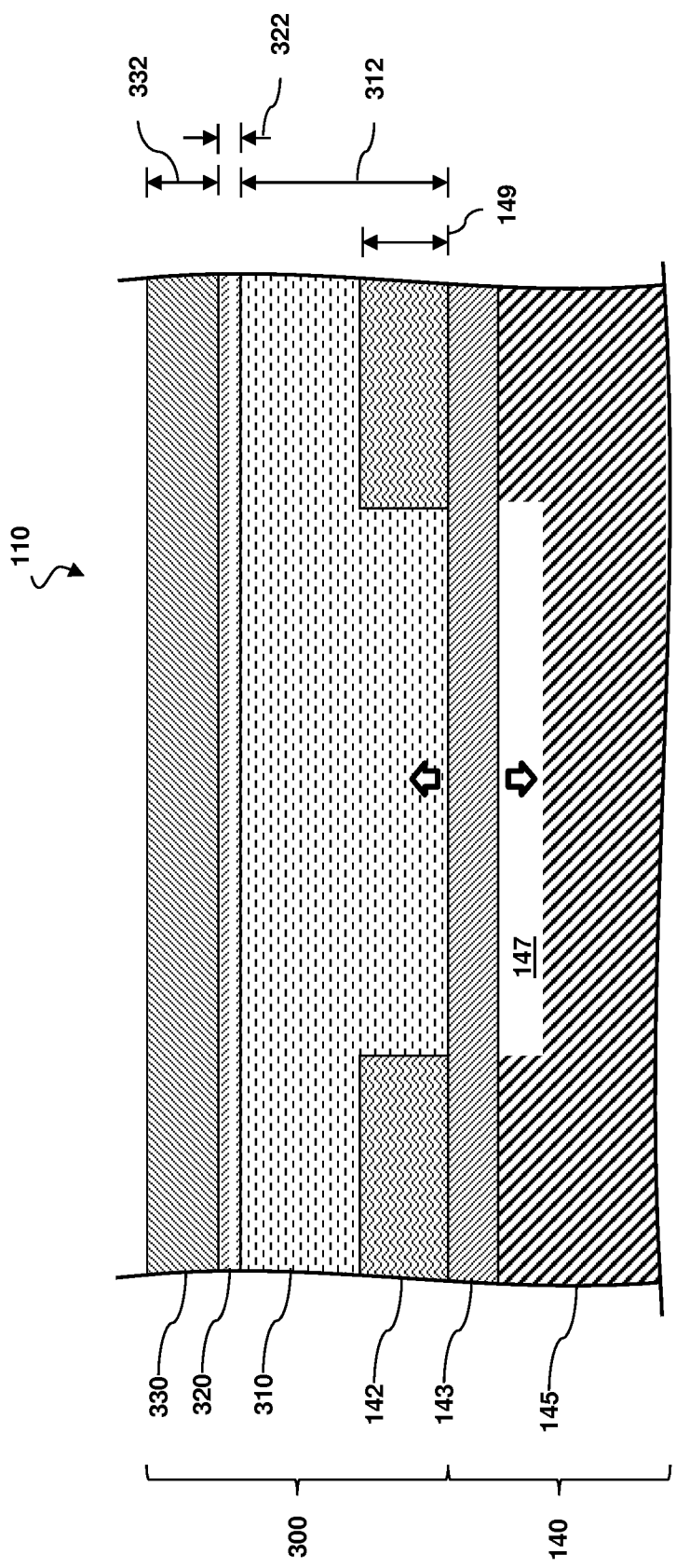
FIG. 3 is a cross-sectional side view of an acoustically-transparent window and an acoustic element of an ultrasound imaging assembly, according to an embodiment of the present disclosure.

FIG. 3 is a cross-sectional side view illustrating a portion of the ultrasound imaging assembly 110. In particular, an acoustically-transparent window 300 is positioned over the acoustic element 140. The acoustically-transparent window 300 can be formed of multiple material layers formed on top of one another, including material layers 310, 320, and/or 330. In that regard, the layers of the acoustically-transparent window 300 can be directly or indirectly coupled, secured, and/or otherwise affixed to another. While only one acoustic element 140 is shown in FIG. 3, it understood that the acoustically-transparent window 300 can be positioned over all acoustic elements 140 of the imaging assembly 110. In general, the acoustically-transparent window 300 facilitates desired propagation of ultrasound energy from the acoustic element 140 to the body lumen 120 of the patient and reflected ultrasound echoes from the body lumen 120 to the acoustic element 140. In that regard, the materials of the acoustically-transparent window 300 provide acoustic impedance values such that the acoustic path for ultrasound energy to and from the acoustic element 140 is free from sharp impedance transitions, which can cause undesirable reflection/refraction. For example, the acoustically-transparent window 300 can provide an acoustic impedance match with the acoustic impedance of blood and/or blood vessel tissue such that ultrasound energy propagates in a desired manner across the transition between the imaging assembly 110 and the blood. CMUT advantageously provides a high bandwidth for ultrasound energy. The materials of the acoustically-transparent window 300 can be advantageously arranged to minimize or eliminate impedance transitions, which reduce bandwidth and prevent the full advantages of CMUT from being realized. In embodiments in which the acoustically-transparent window 300 includes a non-impedance matched layer, that layer is structurally configured to be very thin, such that the layer does not interfere with the desired manner of ultrasound propagation through the window. An additional factor improving acoustic transparency of a material is its low acoustic wave absorption properties (coefficient) in the desired range of acoustic wave frequencies.

As described with respect to FIG. 2, the polyimide interconnect 142 can extend across trenches 144 to couple individual islands 141. In that regard, the interconnect 142 is a mechanical coupling between islands 141. A dimension 149, such as a height or a thickness, of the interconnect 142 can be between approximately 1 µm and approximately 50 µm, approximately 1 µm and approximately 20 µm, approximately 3 µm and approximately 10 µm, including values such as approximately 3 µm, approximately 5 µm, approximately 7 µm, approximately 10 µm, and/or other values both larger and smaller. The acoustically-transparent window 300 can also extend across the trenches 144 such that the acoustically-transparent window 300 is positioned over all acoustic elements 140.

In the orientation of the imaging assembly 110 shown in FIG. 3, layer 330 is the radially outermost layer and is exposed to anatomy within the body lumen 120. Layers 320, 310, as well as the interconnect 142 and the acoustic element 140 are disposed radially inwardly of the layer 330. It is understood that additional components, such as the substrate 132, the acoustic backing material 130, and/or the support member 126 (FIG. 2) are disposed farther radially inwardly of the acoustic element 140.

The acoustic element 140 can be a CMUT element in some instances, including the membrane 143, a substrate 145, and a vacuum gap 147 between the membrane 143 and the substrate 145. The membrane 143 can be formed of silicon nitride in some embodiments. The substrate 145 can include a bottom electrode, and the membrane 143 can include a top electrode. The basic principle of the CMUT element 140 involves a parallel-plate capacitor formed by the top and bottom electrodes 143, 145. The substrate/bottom electrode 145 is fixed, and the membrane/top electrode 143 is flexible. The membrane 143 is configured to deflect, as indicated by the arrows in FIG. 3, during operation of acoustic element 140 to obtain ultrasound data. In receiving mode, an ultrasonic wave (e.g., ultrasonic echoes reflected from the body lumen 120) causes vibration of the membrane 143 and a change of capacitance, which can be detected. In transmitting mode, an alternating voltage is applied between the membrane 143 and the substrate 145. The resulting electrostatic forces cause vibration of the membrane 143, sending out ultrasound energy to the body lumen 120 at the frequency of modulation.

In various embodiments, the acoustic element 140 can be configured to emit ultrasound energy with a center frequency between approximately 1 MHz and approximately 70 MHz, 5 MHz and approximately 60 MHz, or between approximately 20 MHz and approximately 40 MHz, including values such as approximately 5 MHz, approximately 10 MHz, approximately 20 MHz, approximately 30 MHz, approximately 40 MHz, and/or other suitable values both larger and smaller. According to aspects of the present disclosure, the acoustically-transparent window 300 is especially suitable for use with high frequency ultrasound, such as between 20 MHz and 40 MHz, or higher frequencies, for CMUT elements. High frequency ultrasound can be beneficial for B-mode imaging of tissue structures, such as a blood vessel wall, as well fluid within the body lumen 120, such as blood within the blood vessel.

The layer 310 of the acoustically-transparent window 300 is positioned over and directly in contact with the acoustic element 140. In that regard, a bottom surface of the layer 310 is directly in contact a top surface of the membrane 143. The layer 310 can be referenced as the innermost layer of the acoustically-transparent window 300 in that it is the layer radially closest to the acoustic element 140.

The layer 310 can advantageously be formed of a flexible and/or elastic material that is deformable upon movement of the membrane 143. In that regard, the innermost layer (e.g., the layer 310) can be the softest layer of the all of the layers of the acoustically-transparent window 300. In some embodiments, the layer 310 can have a durometer hardness in the Shore 00 range, including values such as less the 5 Shore 00. In some embodiments, the layer 310 can have a durometer hardness between approximately 40 Shore A and 80 Shore A, including values such as approximately 60 Shore A, and/or other suitable values both larger and smaller. The layer 310 can be formed of polybutadiene rubber (PBR) in an exemplary embodiment. The PBR material exhibits one of the lowest acoustic wave abortions in the wide-range of center frequencies used for the intraluminal ultrasound imaging devices. In other embodiments, the layer 310 can include silicone, polyurethane, gel, liquid, combinations thereof, and/or other suitable materials. The layer 310 advantageously allows deflection of the membrane 143 during transmit and receive, and remains in contact with the membrane 143 over the range of the motion of the membrane 143. For example, the layer 310 can be referenced as conformable layer.

The material forming the layer 310 can also advantageously assist with the mechanical dispersion of force. For example, material forming the layer 310 is selected to avoid mechanical coupling and/or contact between the CMUT membrane 143 and any stiff layer in the stack forming the acoustically-transparent window 300. When there is a very soft layer 310 in between, the CMUT membrane 143 does not feel the stiffness of, e.g., the top layer 330. Thus, movement of the membrane 143 during transmit/receive is unaffected. In contrast, if there is a soft but incompressible material surrounded on all sides with a stiff material then movement of the membrane 143 requires movement of the stiff top layer 330, and therefore the membrane 143 is hindered. As described further below, the arrangement of the layers in the acoustically-transparent window 300 also advantageously avoids direct coupling and/or contact between the stiff top layer 330 and the flexible interconnect 142, which would lock in the soft layer 310 and hinder the membrane 143.

The layer 320 of the acoustically-transparent window 300 is positioned over and directly in contact with the layer 310. In that regard, a bottom surface of the layer 320 is directly in contact a top surface of the layer 310. The layer 320 can be harder than the layer 310 but softer than the layer 330. The layer 320 can have a durometer hardness between approximately 5 Shore A and 80 Shore A, including values such as approximately 5 Shore A, 40 Shore A, 60 Shore A, 80 Shore A, and/or other suitable values both larger and smaller. In some instances, the layer 320 can be formed of a material having a greater hardness when the layer 320 is thinner. The layer 320 can be referenced as an adhesive layer or a curing layer in some instances. In the acoustically-transparent window 300, the layer 320 can be a thin bond line between, e.g., the layer 310 and the layer 330. In that regard, the layer 320 can be configured to couple the layer 330 to other layers of the acoustically-transparent window 300, such as the layer 310 in the embodiment illustrated in FIG. 3. In other embodiments, the acoustically-transparent window 300 includes one or more additional layers between the layers 310 and 320. The one or more additional layers, together with the layers 310, 320, and 330 can advantageously provide a desired acoustic impedance transition from the acoustic element 140 to the body lumen 120.

The layer 320 can be formed of polyurethane (PU) in an exemplary embodiment. The acoustic impedance of PU can be $Z=1.3$ to 1.9. In other embodiments, the layer 320 can include a silicone or other soft conformable material. In some instances, PU can be advantageous because it can be implemented as a relatively thin line with good impedance values for acoustic matching, whereas other materials, such as silicone, may require filling to increase impedance for acoustic matching, which correspondingly increase a dimension 322, such as height or thickness, of the layer 320. PU can be used for applications in which minimizing diameter of the intravascular device 102 is a priority. In some embodiments, the acoustically-transparent window 300 does not include the layer 310. Instead, the layer 320 is positioned over and in direct contact with the acoustic element 140. In such instances, the layer 320 is the innermost layer of the acoustically-transparent window 300. As similarly described above, the layer 320 can advantageously be a flexible and/or elastic material that is deformable upon movement of the membrane 143. When the layer 310 is omitted in the acoustically-transparent window 300, a softer PU can be used. A harder PU can be used when the layer 310 is positioned between the layer 320 and the acoustic element 140. The layers 310 and/or 320 can advantageously provide a low attenuation and matched impedance for ultrasound energy.

A dimension 312, such as a height or a thickness, of the layer 310 can be between approximately 10 µm and approximately 20 µm, or between approximately 12 µm and approximately 18 µm, including values such as approximately 10 µm, approximately 13 µm, approximately 15 µm, approximately 17 µm, and/or other values both larger and smaller. The dimension 322, such as a height or a thickness, of the layer 320 can be between approximately 1 µm and approximately 10 µm, or between approximately 1 µm and approximately 5 µm, including values such as approximately 1 µm, approximately 3 µm, approximately 5 µm, and/or other values both larger and smaller. Together, the total height or thickness of the layer 310 and the layer 320 can be greater than approximately 15 µm, such as approximately 20 µm.

The layer 330 of the acoustically-transparent window 300 is positioned over and directly in contact with the layer 320. In that regard, a bottom surface of the layer 330 is directly in contact a top surface of the layer 320. The layer 330 can be referenced as the outermost layer of the acoustically-transparent window 300 in that is the layer radially farthest from the acoustic element 140. The outermost layer 330 can be opposite the innermost layer 310 in the embodiment of the acoustically-transparent window 300 illustrated in FIG. 3. The layer 330 is exposed to anatomy within the body lumen 120 (e.g., blood, blood vessel tissue, stenosis). A dimension 332, such as a height or a thickness, of the layer 330 can be between approximately 1 µm and approximately 10 µm, or between approximately 3 µm and approximately 8 µm, including values such as approximately 1 µm, approximately 3 µm, approximately 5 µm, 7 µm, and/or other values both larger and smaller.

The layer 330 can be advantageously formed of a relatively more rigid material. In that regard, the outermost layer (e.g., layer 330) can be the hardest layer of the all of the layers of the acoustically-transparent window 300. The layer 330 can have a durometer hardness between approximately 1 Shore D and 100 Shore D, approximately 80 Shore D and 100 Shore D, including values such as approximately 85 Shore D, and/or other suitable values both larger and smaller. The arrangement of the layers 310, 320, and 330 provide mechanical, electrical, and/or chemical protection for the acoustic element 140. Mechanical protection can be needed, e.g., while the intraluminal imaging device 102 comes into contact with anatomy. When the acoustically-transparent window 300 encounters rigid or sharp anatomy, such as a when the intraluminal imaging device 102 crosses a calcified stenosis, the soft bottom layer 310 deforms but the tough top layer 330 stays intact. The top layer 330 also has a high breakdown voltage for electrical protection. Additionally, the layer 330 also provides good permeation barrier for water.

The layer 330 can be formed of polyethylene terephthalate (PET) in an exemplary embodiment. In other embodiments, the layer 330 can include a polymer material, such as polymethylpentene (PMP) or TPX®, available from Mitsui Chemicals. In some instances, PET can be used when a thinner layer 330 is desired, such as when minimizing diameter of the intravascular device 102. A thinner PET layer 330 advantageously allows the propagation of ultrasound energy in the desired manner, e.g., without reflections, even though PET is not impedance matched. PMP or TPX® can be used in applications where a thicker layer 330 is beneficial. A PMP layer 330 is impedance matched and can therefore be thicker without causing undesirable ultrasound reflections. In some embodiments, the layer 330 can be obtained, prior to assembly of the intraluminal imaging device 102, in the form of tubing, such as shrink wrap tubing. In other embodiments, the layer 330, prior to assembly of the intraluminal imaging device 102, can be in the form of a planar sheet of material (e.g., a foil) that can be wrapped into an annular configuration around the longitudinal axis LA, around the array 124 of acoustic elements 140.

In embodiments in which a PET heat shrink tube is used as the tough upper layer 330, the dimension 332, such as height or thickness, is selected to be small compared to the wavelength of sound, preferably <1/10 λ. The acoustic wavelength in PET is close to 80 µm at 30 MHz. While PET is not impedance matched in that it has a relatively higher acoustic impedance, PET heat shrink tubings with a dimension 332, such as wall thickness, of approximately 5 µm (e.g., available from Vention Medical) minimize acoustic reflections at impedance transitions. The thinner the not-impedance-matched layers are, the better the acoustic performance at higher frequencies. In other application, an impedance-matched material, such as TPX®, is used as the outer protective layer 330. In that case, no acoustic reflections (reverb) will occur even when the layer 330 is relatively thicker.

The arrangement of the layers 310, 320, 330 advantageously prevents direct contact between the layer 330 and the interconnect 142. Direct contact between relatively harder layer 330 and the interconnect 142 would eliminate the movement/conformance of the layer 310 with the membrane 143 during ultrasound transmit and receive. In that regard, the dimension 312 of the layer 310 is selected such that the layer 310 positioned over and directly in contact with interconnect 142, as well as the membrane 143. In that regard, a bottom surface of the layer 310 is directly in contact a top surface of the interconnect 142. Accordingly, the layer 310 and/or the layer 320 is positioned between the layer 330 and the interconnect 142. In embodiments of the imaging assembly 110 with configurations other than F2R, such as those without the flexible interconnect 142, the entirety of the bottom surface of the layer 310 can be in contact with the top surface of the membrane 143.

The present disclosure provides numerous advantages compared to acoustically-transparent windows for ultrasound applications known in the art. In that regard, the arrangement of the acoustically-transparent window 300 described herein can be utilized for a wide-range of center frequencies, such as a 5 MHz and 40 MHz, whereas existing windows where described in the context of 1 MHz to 20 MHz. As described herein, layers 310, 320, 330 provide a suitable acoustic pathway even for high frequency ultrasound energy (e.g., 20 MHz to 40 MHz). Existing acoustic windows in the art are also much thicker (e.g., >30 µm), as well as designed for re-usable devices, such as external ultrasound probes. Aspects of the present disclosure advantageously provide a thin acoustically-transparent window 300 suitable for intraluminal applications, such as IVUS imaging. In that regard, the acoustically-transparent window 300 also is arranged implementation in a flex-to-rigid framework, such as being positioned over the polyimide interconnect 142, which allows for the array 124 to be transitioned from a planar configuration to an annular configuration around the longitudinal axis LA of the device 102 Known acoustic windows for external ultrasound probes do not address the need to avoid contact between the tough outer layer 330 and the interconnect 142.

In some embodiments, the adhesive layer 320 is the hardest layer of the acoustically-transparent window 300. Such embodiments can permit propagation of ultrasound energy through the acoustically-transparent window 300 in the intended manner by making the adhesive layer 320 very thin, even though the impedance of the layer 320 is likely undesirably high with a very hard material. In a two layer design of the acoustically-transparent window 300, the outer layer will be harder than the inner layer. In some instances, a hydrophilic coating is positioned over the acoustically-transparent window 300 The hardness of the hydrophilic coating can be greater than or less than hardness of the layers 310, 320, and/or 330 of the acoustically-transparent window 300, in various embodiments.

According to one advantageous set of embodiments, a thickness of the acoustically-transparent window may vary across its extent.

Thickness means for example the dimension normal to a surface of the window, or of the acoustic elements or of the flexible elongate member. It means for example a dimension in the direction extending between the innermost layer and the outermost layer. It means for example a height of the acoustically transparent window.

This set of embodiments will now be explained in more detail.

As described above, embodiments of the present invention are based on providing an outermost layer for the acoustically-transparent window which is the hardest of the layers, and an innermost layer which is the least hard of the layers. The benefit of a mechanically hard and strong outermost layer is that it provides mechanical protection for the softer lower layers, for example for the softer innermost layer, whose softness advantageously enables free unimpeded movement of the acoustic elements while still providing coupling between the window and the elements. For example, the hard outermost layer provides scratch protection for the lower layers, for example in the case of the flexible elongate member passing over a calcified stenosis.

However, some example hard materials which may advantageously be used for the outermost layer can exhibit a somewhat poor acoustic match to water or blood, which can lead to a significant ringing effect in the obtained acoustic signal. This reduces the bandwidth and the axial resolution. This in turn can significantly degrade the obtainable image quality. By way of one example, the example material PET, which is one advantageous suitable material for forming the outermost layer, exhibits a poor acoustic match with blood and water, leading to problems such as those described.

To explain the problem further, by way of one illustrative example, the disadvantageous ringing effect for one example set of acoustic window layer materials will now be described. This represents only one example, and the problem may also similarly arise for other sets of layer materials.

By way of this example, one advantageous set of materials for the acoustically-transparent window, starting from the innermost layer and working outward, is PBR-PU-PET (Polybutadiene-Polyurethane-Polyethylene terephthalate). The material properties of these materials compared with water are shown in Table 1 below:

TABLE 1

|       | Speed [m/s] | Density [kg/m3] | Impedance [MRayl] |
|-------|-------------|-----------------|-------------------|
| PBR   | 1576        | 927             | 1.46              |
| PU    | 1567        | 1050            | 1.65              |
| PET   | 2560        | 1390            | 3.56              |
| Water | 1500        | 1000            | 1.50              |

The hard PET foil layer has an acoustic impedance of Z=3.6 MRayl, compared to water which has an acoustic impedance of Z=1.5 MRayl. Thus, a strong reflection, of both outgoing and incoming ultrasound waves, of 41% results at the PET layer.

Figure 4:
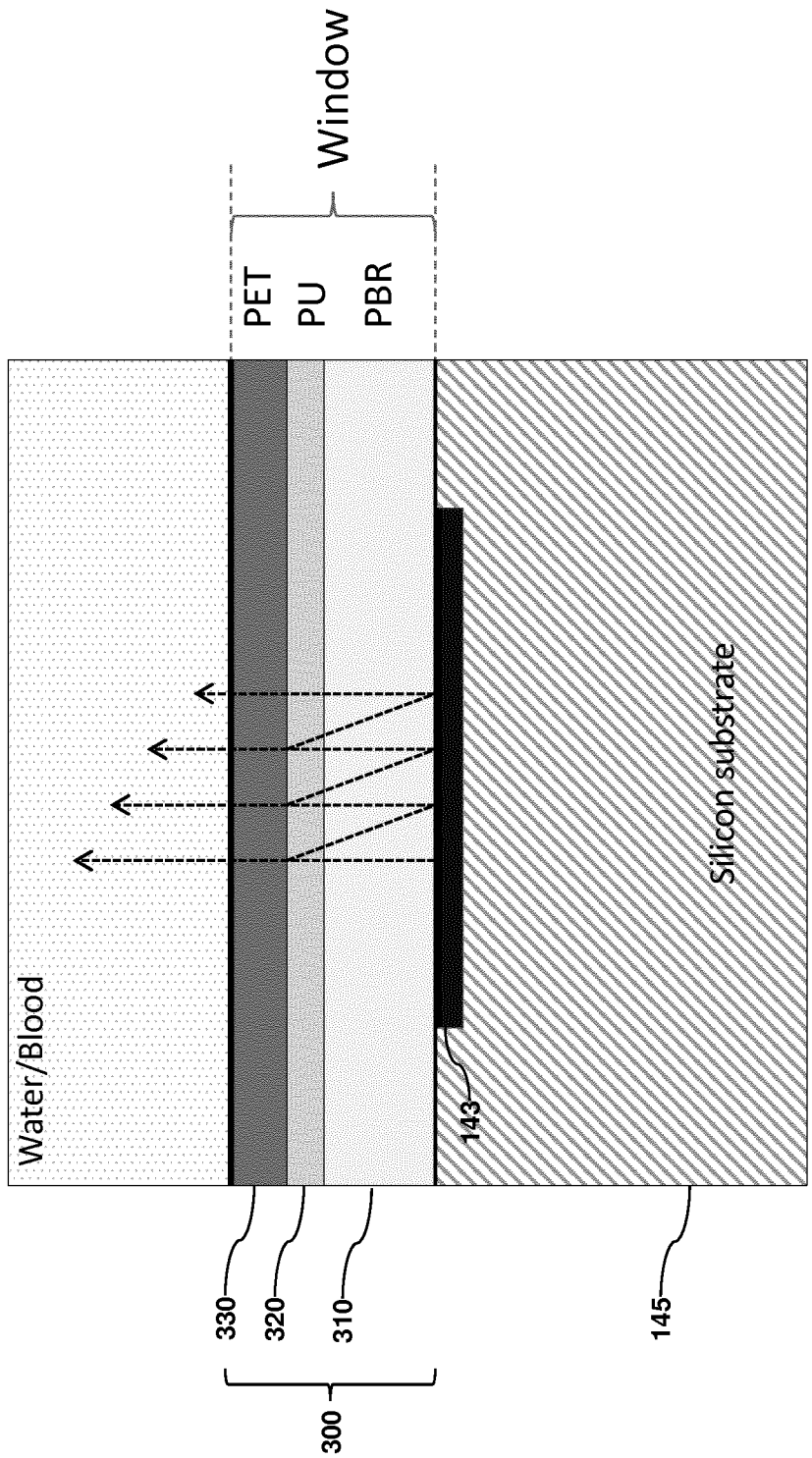
FIG. 4 illustrates reflection of acoustic waves at a PET layer of an example acoustically-transparent layer.

This is illustrated schematically in FIG. 4, which shows the PBR innermost layer 310, the PU adhesive layer 320 and the PET outermost layer 330 of the acoustically transparent window 300, coupled atop an example CMUT element membrane 143, mounted to a silicon substrate 145. The reflection of outgoing acoustic signals is illustrated.

This strong reflection is visible as a tail in the echo signal, or a 'hump' in the obtained ultrasound spectrum.

Figure 5:
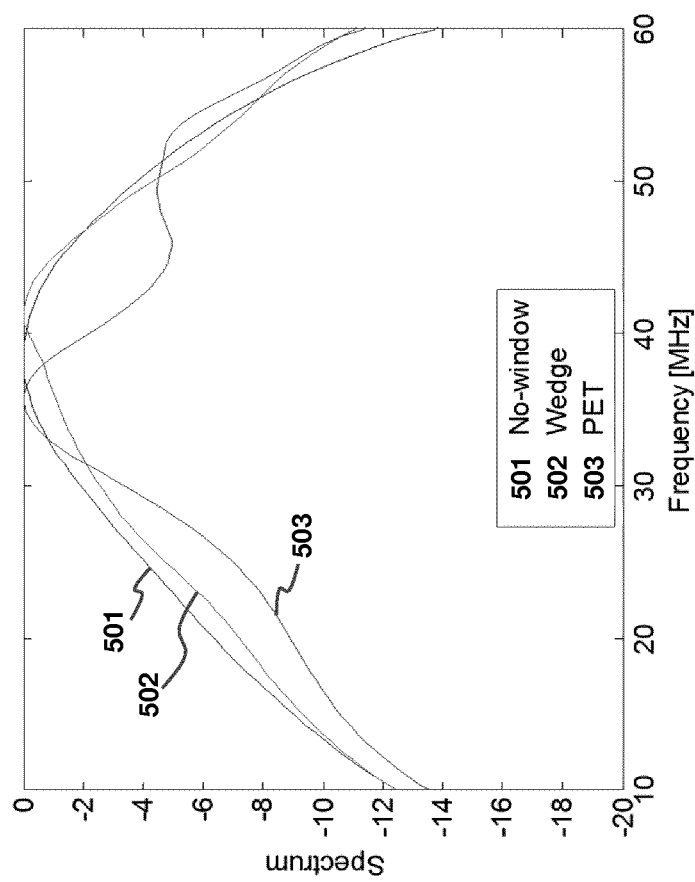
FIG. 5 illustrates an obtainable ultrasound signal spectrum for different acoustic window configurations.

This effect is illustrated in the graph of FIG. 5.

The graph represents the achieved ultrasound signal spectrum for a CMUT ultrasound transducer having a central (mean) frequency output of 40 MHz.

Curve 501 represents the spectrum (calculated by the finite element method) for the CMUT transducer in the absence of a window. This curve represents the ideal, desired spectrum, since it shows the signal in the absence of any reflection or interference effects of a window. The equivalent time domain signal has a short tail.

Curve 503 represents the FEM calculated ultrasound spectrum for the case in which the three layer PBR-PU-PET window, including PET layer, is present. A 'hump' can be observed in the obtained spectrum at around 35 MHz. This is caused by a resonance effect due to the strong reflection mentioned above. This effect is highly undesirable as it degrades the image quality.

To ameliorate this problem, according to advantageous embodiments of the present invention, the acoustically-transparent window is provided having a thickness which varies across its extent (i.e. across its major cross-sectional area). By way of example, the acoustically-transparent window may be provided having a thickness which varies such that the window defines a wedge shape.

The thickness variation causes the ringing in the tail of the spectrum to average. As a result, the spectrum curve is smoothed, and the 'hump' is substantially eliminated.

This is illustrated by curve 502 in FIG. 5. Curve 502 shows the obtained ultrasound spectrum using a wedge shaped acoustically-transparent window. As can be seen, the shape substantially eliminates the interference/reflection effects and the spectrum approaches the shape of the desired (ideal) no-window curve 501.

Figures 6A, 6B:
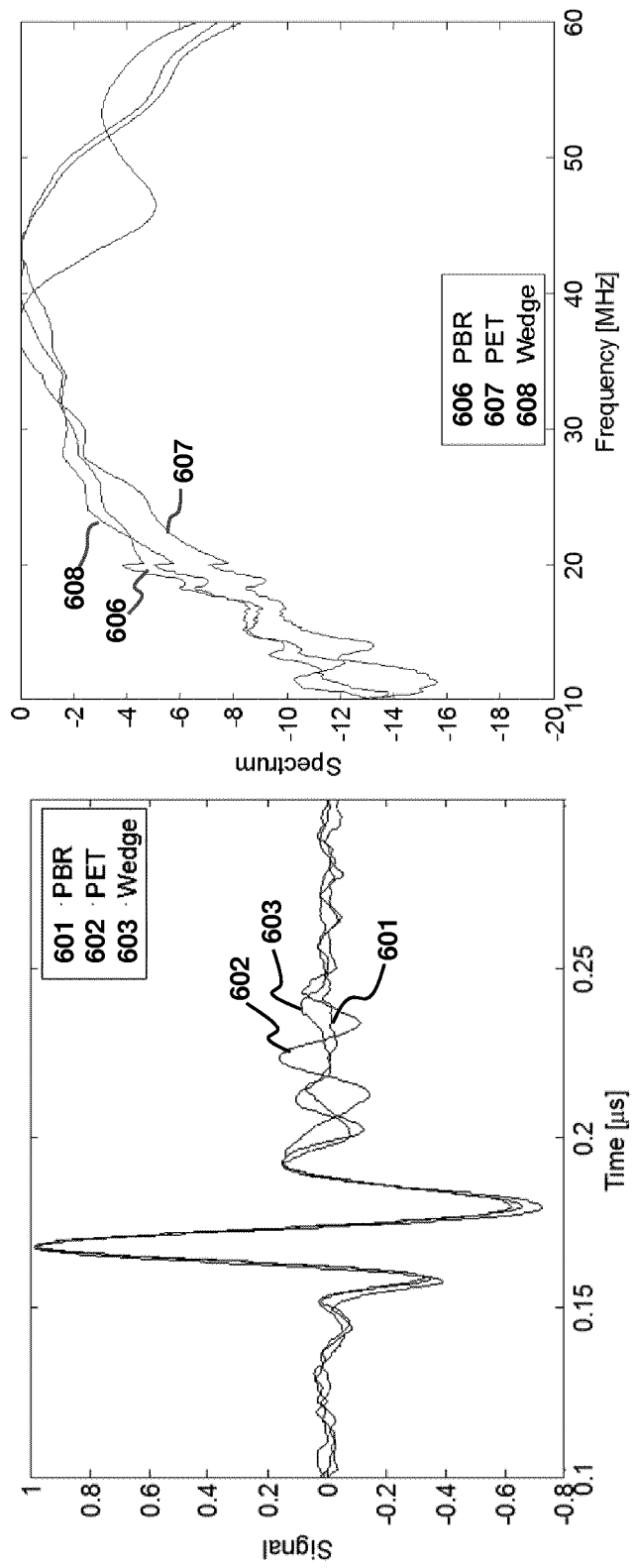
FIG. 6 illustrates obtaining ultrasound signals and signal spectra for different window configurations.

Further experimental results are shown in FIGS. 6A and 6B. FIG. 6A shows by way of illustration the obtained ultrasound signal as a function of time [µs] for a CMUT transducer covered by each of the following: a PBR only material layer 601, a PBR-PET material layer stack 602, and a complete acoustically-transparent window having a wedge shape 603. FIG. 6B shows the obtained ultrasound spectrum as a function of frequency [MHz], for each of a PBR-only material layer 606, a PBR-PET material layer stack 607, and a complete acoustically-transparent PBR-PU-PET window having a wedge shape 608.

It can be seen that the spectrum 608 for the wedge-shaped window resembles the (ideal) PBR-only spectrum 606. The obtained bandwidth is >50%. When PET is added to the material stack, without wedge shape formation, the obtained spectrum 607 exhibits the undesirable hump, and the bandwidth is reduced to around 25%.

Different options are possible for the particular configuration of the variable thickness acoustically-transparent window.

According to a preferred set of examples, the thickness of the acoustically-transparent window varies smoothly across the window, such that an uppermost surface of the window (i.e. of the outermost layer) inclines or declines smoothly at one or more rates or incline angles across the window.

The thickness may vary linearly, so that the upper surface of the window slopes linearly at one or more slope angles.

Figure 7:
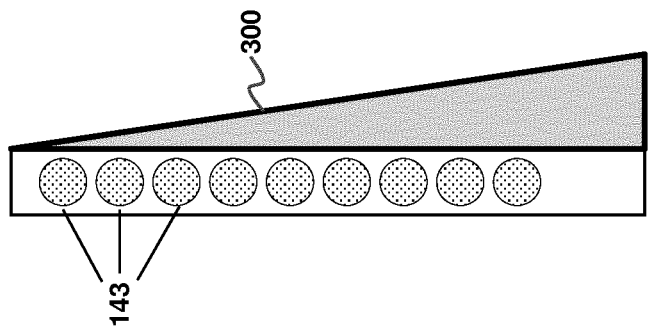

FIG. 7 schematically depicts a side cross-sectional view through one example arrangement which follows this configuration. The acoustically transparent window 300 is shown extending over an array of ultrasound acoustic elements 143. In this example, the plurality of acoustic elements 143 is arranged as an array of elements, comprising a plurality of rows (lines) of elements. One line of acoustic elements 143 is schematically drawn in FIG. 7.

In this example, the acoustically-transparent window is arranged such that the thickness of the acoustically-transparent window varies along a direction of the lines (rows) of acoustic elements, i.e. the uppermost surface of the window (i.e. of the outermost layer) slopes in a direction parallel the lines or rows of acoustic elements 143.

In alternative examples, the thickness may vary non-linearly, so that the upper surface curves smoothly up or down at one or more rates. Where the acoustic elements comprise an arrangement of one or more lines of elements, the sloping of an uppermost surface of the element may extend along the direction of said one or more lines of elements.

As mentioned above, where the plurality of acoustic elements comprises an array of elements comprising one or more rows, the thickness of the window may vary along a direction of said one or more rows.

In the particular example of FIG. 7, the sloping of the acoustically-transparent window is such that the acoustically transparent window 300 follows a wedge shape.

According to one or more examples, the thickness of the acoustically-transparent window may vary along the direction of the longitudinal axis of the flexible elongate member. This may coincide with a direction of the lines or rows of acoustic elements in some examples, so that the thickness varies (e.g. slopes or inclines) along the direction of both.

According to one or more embodiments, the thickness of the acoustically-transparent window may oscillate smoothly between a lower and upper thickness level, such that an uppermost surface of the outermost layer varies up and down across the layer between an upper and lower surface level.

Figure 8:
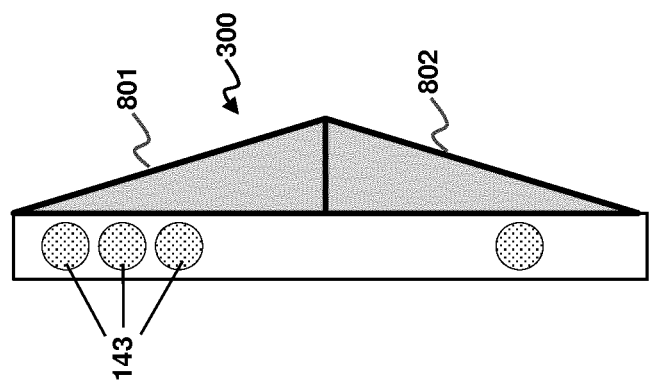

An example is schematically depicted in FIG. 8.

In this example, the thickness of the acoustically-transparent window 300 oscillates linearly, such that an uppermost surface of the window (i.e. of the outermost layer) slopes linearly up and down between an upper and lower surface level. This results, in the example of FIG. 8, in a window comprising two sloped sections 801, 802, one section 801 which respectively inclines toward a central peak thickness point, and one 802 which declines away from the peak thickness point (or equivalently, both inclining or declining respectively toward or away from this central peak).

FIG. 9 schematically depicts a further example. In this example, the thickness of the acoustically-transparent window 300 oscillates linearly a number of times across the extent of the window between a minimum and maximum thickness level. This shows as a linear sloping of an uppermost surface of the window (i.e. of the outermost layer) of the element up and down between an minimum and maximum surface level. This results in a total of six sloped sections 901-906, which respectively slope upwards and downwards towards and away from peak thickness points of the window 300.

For the variable thickness window to be effective in suppressing the resonance or ringing effect (and the consequent hump in the ultrasound signal spectrum), the distance z at which an target observed point of the anatomy is scanned (relative to the imaging assembly of the intraluminal device) should be sufficiently large for the acoustic 'averaging' effect of the window to take effect. Where the point of observation is very close to the imaging assembly, only a small part, δ, of the array of acoustic element contributes.

Figure 10B:
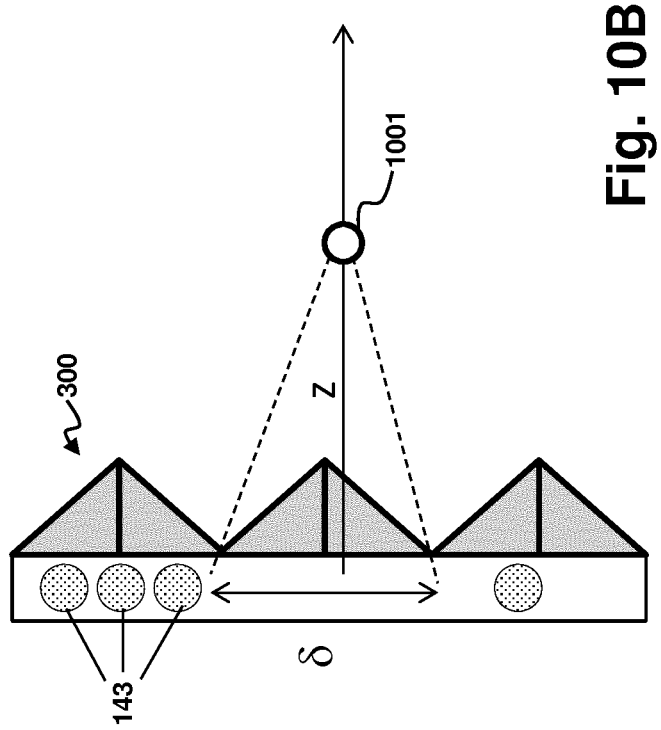
FIG. 10 illustrates observation distance dependency for effective utilization of a variable thickness acoustically transparent window for eliminating resonance effects.
Figure 10A:
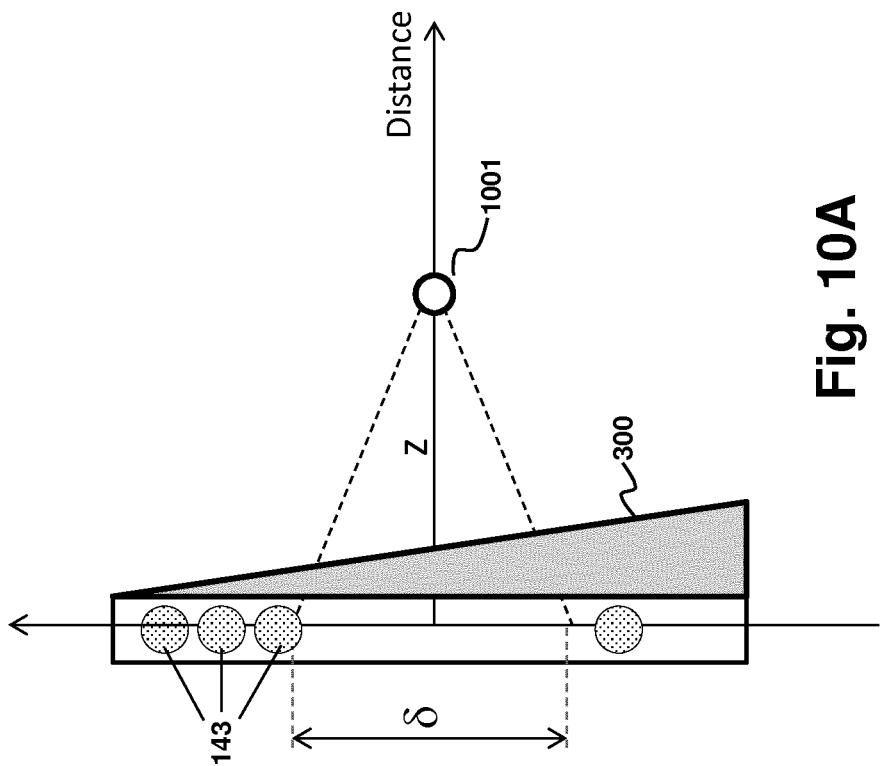

This is schematically depicted in FIGS. 10A and 10B, which show observation of an observed point 1001 with two different respective variable thickness windows 300, where the observed point is a distance, z, from the plurality of acoustic elements 143.

Hence, to enable observation of points at even close distances relative to the imaging assembly, the variable thickness acoustic window should be steep enough in its thickness gradient, such that there is sufficient thickness variation along δ to be effective.

A preferred distance for viewing objects is the near-field distance, $z_0$. The near field distance is the distance at which a plane wave is first being formed. Obtained images are sharpest for objects observed at the near-field distance. However, objects can also be viewed at distances other than the near-field distance.

The approximate relation between the near-field distance, $z_0$, and δ is:

$$z_0 = \frac{\delta^2}{4\lambda}$$

where λ is wavelength of the sound waves,

For example, for c=1500 m/s, f=40 MHz, and δ=600 microns, the resulting near-field distance is $z_0$=2.4 mm, where c is the speed of sound in the medium separating the imaging assembly and the observed point 1001.

For this example configuration, a plane wave is created, and the full array of acoustic elements contribute to the signal, so long as the object is viewed at or close to the near-field distance of 2.4 mm. Hence also the entire length of the acoustic window contributes to suppress the resonance. A distance of 2.4 mm is within the range of typical observation distances for the device during typical uses.

By way of example, the acoustic window thickness may vary across its full length or extent between a starting thickness of approximately 10 microns and a final thickness of approximately 30 microns. The thickness may increase linearly from 10 to 30 microns across its full extent for example. This provides a sufficient thickness gradient for observation of objects at observation distances z>$z_0$, where z is the observation distance and $z_0$ is the near-field distance, as discussed above.

This however represents one example thickness gradient only however, and others may alternatively be used.

For example, simulations have been performed to test different thickness gradients in terms of their performance in eliminating the ringing effect (i.e. the tail in the echo signal) discussed above. Based on these simulations it has been found that windows in which the thickness increases linearly by a total of approximately 20-30 microns across the full length of (at least the active part, δ, of) the window element can be expected to perform best. For example, the window may advantageously vary (e.g. linearly increase) in thickness from an initial thickness of between 7-15 microns to a final thickness of between 20-30 microns.

In preferred examples, the starting thickness of the wedge window (i.e. the thickness at the window's thinnest point, at one end of the window) should ideally be as small as possible to minimize acoustic attenuation. It has been found that a starting thickness of approximately 10 microns (for example between 7 and 15 microns) is optimal, in terms of balancing acoustic performance, and structural stability.

Figure 11:
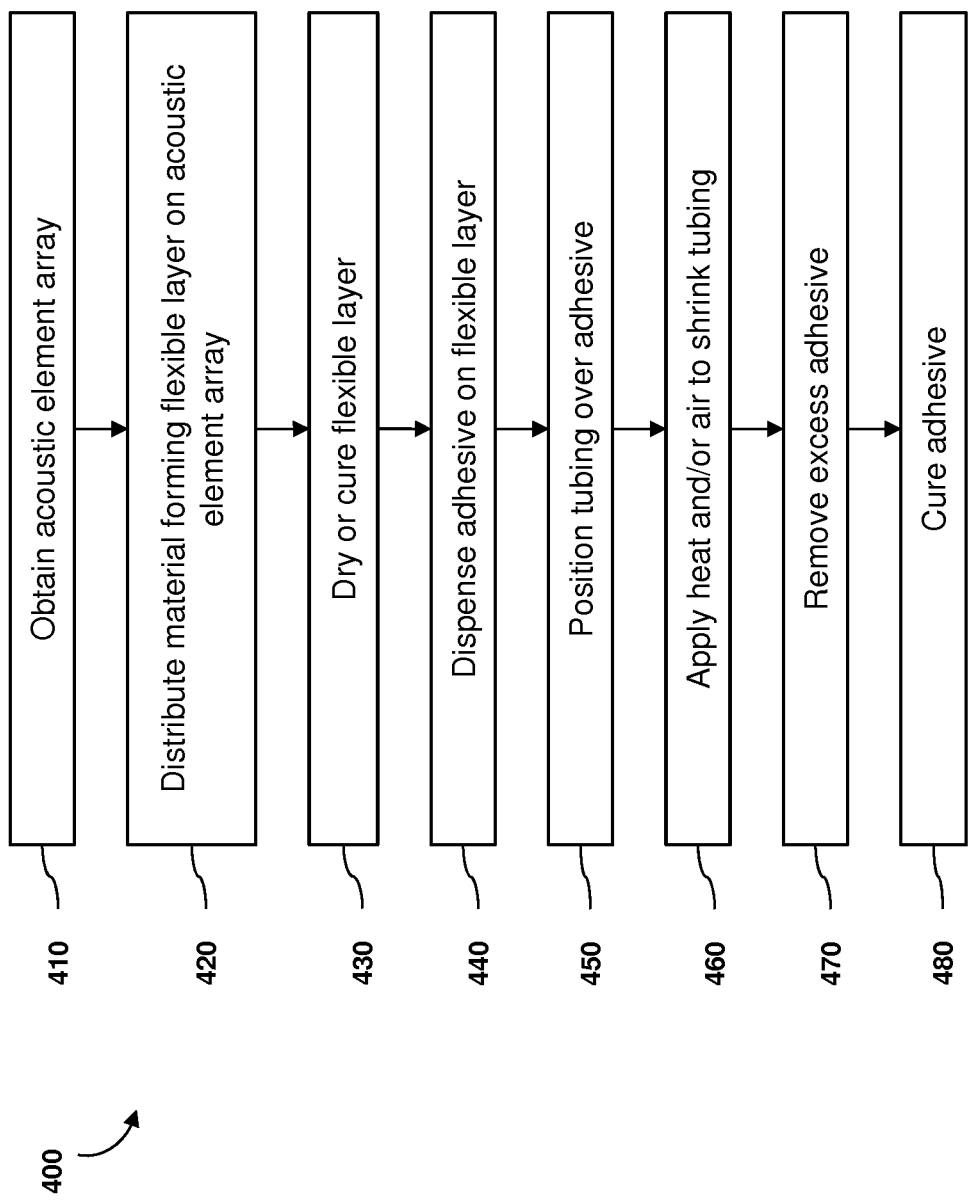
FIG. 11 is a flow diagram chart of a method of manufacturing an intraluminal ultrasound imaging device, according to an embodiment of the present disclosure.

FIG. 11 is a flow diagram of a method 400 of manufacturing at least portions of the intraluminal ultrasound imaging device 102, according to an embodiment of the present disclosure. As illustrated, the method 400 includes a number of enumerated steps, but embodiments of the method 400 may include additional steps before, after, and in between the enumerated steps. In some embodiments, one or more of the enumerated steps may be omitted, performed in a different order, or performed concurrently. The steps of the method 400 can be carried by a manufacturer of the device 102 to yield the devices including features described in FIGS. 1-3. The method 400 will be described with reference to FIGS. 12-17, which are diagrammatic views of various components of the device 102 during various steps of manufacturing. For example, FIGS. 12-17 illustrate assembly steps for various components of ultrasound imaging assembly 110, such as the acoustically-transparent window 300 disposed over the acoustic element array 124.

Figure 12:
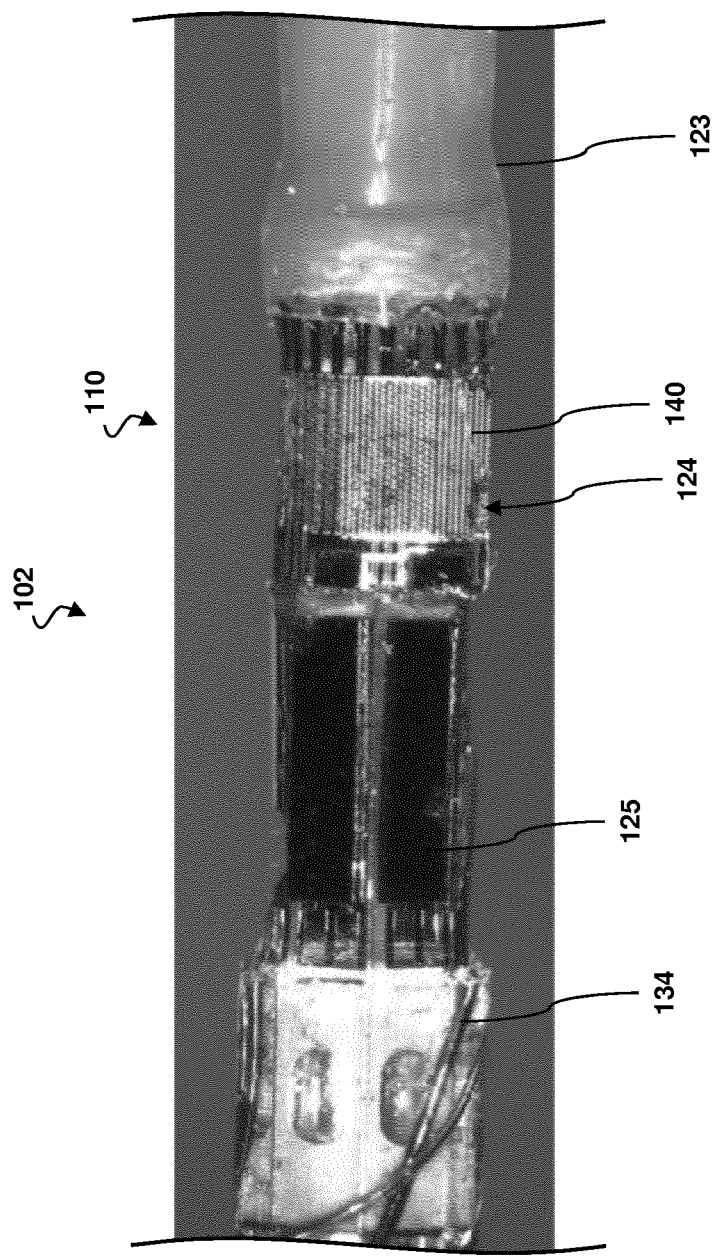
FIGS. 12-17 are diagrammatic views of an ultrasound imaging assembly during various steps of the method of manufacturing of FIG. 11.

At step 410, the method 400 includes obtaining an acoustic element array (FIG. 11). A diagrammatic top view of an acoustic element array 124 is illustrated in FIG. 12, according to an embodiment of the present disclosure. The acoustic element array 124 can include a plurality of acoustic elements 140. In an exemplary embodiment, the acoustic elements 140 can be CMUT elements. The imaging assembly 110 of the device 102 shown in FIG. 12 also includes the tip member 123 positioned distally of the array 124, the controllers 125 positioned proximally of the array 124, and the communication lines 134 (e.g., conductors providing electrical communication) extending proximally from the controllers 125.

At step 420, the method 400 includes distributing material forming a flexible layer of the acoustically-transparent window over and directly contacting the acoustic element array (FIG. 11). For example, PBR can be used to form the innermost layer 310 (FIG. 3). In that regard, dissolved PBR can be dispensed on to device 102. The device 102 can be rotated (e.g., around the longitudinal axis LA) after the PBR is dispensed or the PBR can be dispensed while the device 102 is rotating. As a result, the PBR is spread evenly around the circumference of the array 124 and/or other components of the device 102. In some embodiments, heptane is added to PBR to control viscosity of the dissolved material.

At step 430, the method 400 includes drying or curing the flexible layer of the acoustic window. In embodiments in which heptane is added to the PBR, the step 430 can include evaporating the heptane. Step 430 can include applying heat or air to the material forming the flexible layer. As a result of step 430 the material distributed in step 420 forms into the layer 310. As a result of drying/curing the layer 310 separately from forming the others layers, the dimension 312, such as height or thickness, of the layer 310 (FIG. 3) can be controlled independently of the steps involved in forming the other layer. For example, the dimension 312 of the layer 310 does not depending on the shrinking behavior of the tubing forming the layer 330, as described with respect to step 460.

Figure 13:
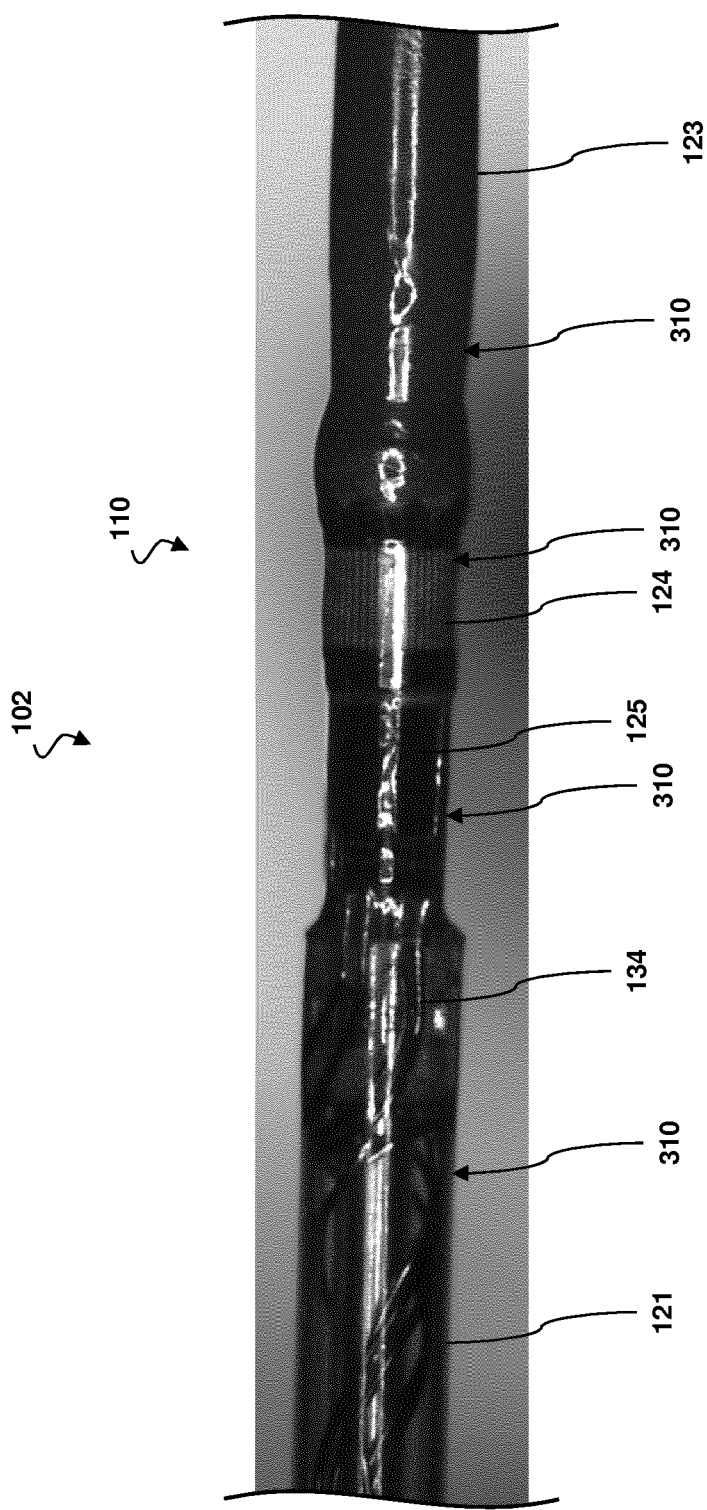

FIG. 13 illustrates the imaging assembly 110 of the device 102 after step 430. FIG. 13 is a diagrammatic top view after the flexible layer of the acoustically-transparent window has been distributed over the acoustic element array and cured, according to an embodiment of the present disclosure. In that regard, the layer 310 is completely covers the array 124. In the illustrated embodiment of FIG. 13, the layer 310 also covers at least a portion of the tip member 123, the controllers 125, and/or the communication lines 134. In that regard, the layer 310 can form part of the flexible elongate member 121.

In embodiments in which additional layers can form part of the acoustically-transparent window 300, the method 400 includes forming additional layers over the flexible layer 310.

Figure 14:
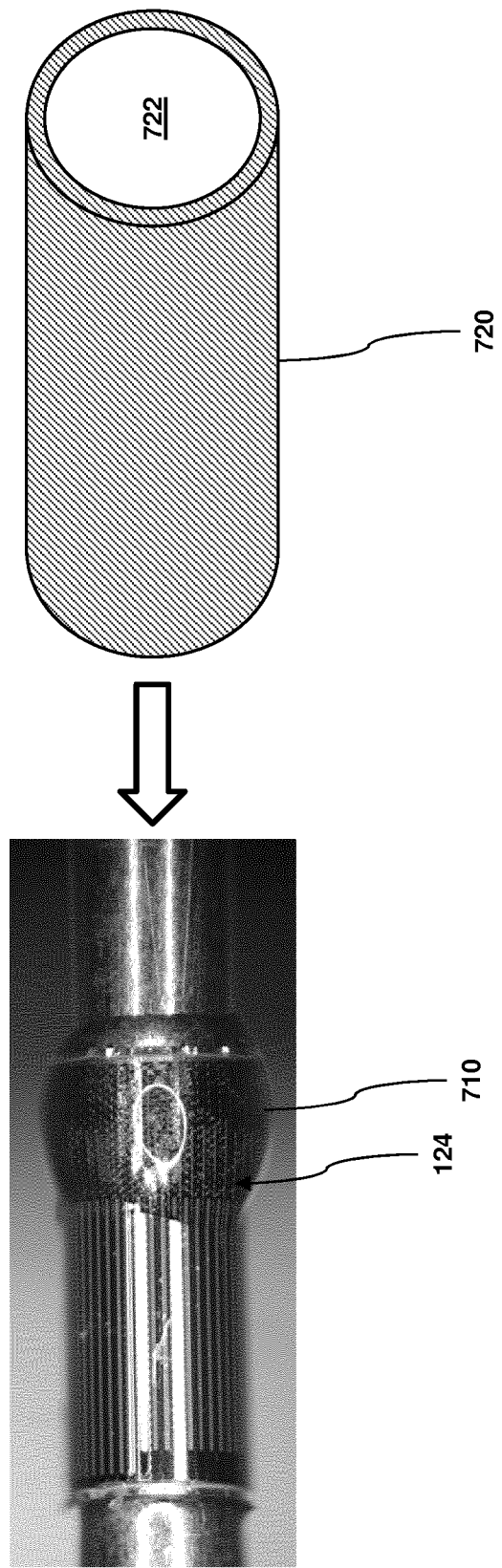

At step 440, the method 400 includes dispensing an adhesive on the flexible layer (FIG. 11). The adhesive, such as PU, can form the layer 320 between the layers 310 and 330 (FIG. 3). For example, one or more droplets of the adhesive can be dispensed directly onto the dried/cured layer 310. In embodiments of the acoustically-transparent window 300 that omit the layer 310, the adhesive can be disposed directly onto the array 124. FIG. 14 illustrates a volume 710 of the adhesive dispensed over the array 124. FIG. 14 is a diagrammatic top view of the heat shrink tubing arranged to be positioned over the acoustic element array (step 450) including the adhesive dispensed on the flexible layer of the acoustically-transparent window, according to an embodiment of the present disclosure. In some embodiments, the adhesive is sprayed onto the layer 310 and/or the array 124.

At step 450, the method 400 includes positioning tubing over the adhesive and the acoustic element array (FIG. 11). The tubing can form the outermost layer 330 (FIG. 3) in some instances. In that regard, the tubing can be a heat shrinkable tubing formed of PET in some embodiments. As shown in FIG. 14, the tubing 720 can include lumen 722. The array 124 and/or the tubing 720 is moved such that the array 124, with the volume 710 of the adhesive disposed thereon, is positioned within the lumen 722 of the tubing 720.

In some embodiment, the step 450 also includes fixing the ends of the heat shrink tubing 720. In that regard, during the heat shrink process, the wall thickness increases if the tube 720 can freely shrink (reduced diameter, reduced length, increased wall thickness). The increase in all thickness can be minimized or eliminated by fixing the heat shrink tube 720 so it cannot shrink in the length or longitudinal direction. Another option for step 450 is to mount the tube 720 around the array 124 by stretching the tube 720 in the length direction so that it shrinks in diameter prior to heating. In some instances, stretching the tube 720 prior to heating can even lead to a thinner wall after applying heat. For example, the dimension 332 of the layer 330 can be smaller.

In embodiments in which tubing is not used, the step 450 includes positioning a planar piece of material (e.g., a foil) around the array 124 and the volume 710 of the adhesive. For example, the planar piece of material can be wrapped into an annular configuration around the array 124 and the volume 710 of the adhesive.

At step 460, the method 400 includes applying heat and/or air to shrink the tubing (FIG. 11). For example, as a result of applying hot air, the tubing 720 shrinks around the array 124 forming the rigid layer 330 (FIG. 3). The shrinking tubing 720 spreads out the adhesive laterally, between the layer 310 and the surface of the lumen 722. The volume 710 of the adhesive is thus distributed around the entire circumference of the layer 310, rather than remaining the droplet form shown in FIG. 14. In embodiments, in which the tube 720 is stretched (step 450), the step 460 can include a combination of applying heat and mechanical stretching. Excess tubing 720 can be cut and removed if needed. The cut ends of the tubing 720 can be additionally heat shrunk. In some instances, additional adhesive is applied around the ends of the tubing 720.

In embodiments which omit the layer 310, the adhesive is spread out laterally, between the array 124 and the surface of the lumen 722 as a result of shrinking tubing 720. Adhesive is thus distributed around the entire circumference of the array 124.

At step 470, the method 400 includes removing excess adhesive (FIG. 11). The shrinking tubing 720 can expel excess adhesive from the space between the layer 310 and the surface of the lumen 722, out of the ends of the tubing 720. The excess adhesive can be removed, such as by wiping away, prior to curing the adhesive (step 480).

At step 480, the method 400 includes curing the adhesive (FIG. 11). In some embodiments, the adhesive is a two component curing systems, such as a two component PU. Step 480 can include application of heat and/or air. In some embodiments, the adhesive cures without vapor emission. Solvent evaporation or gases formed by, for instance, moist curing can be advantageously avoided. If something evaporates in/from the glue layer 320, gas/air bubbles will be formed under the layer 330 and trapped in the acoustically-transparent window 300, thereby degrading acoustic performance.

Figure 15:
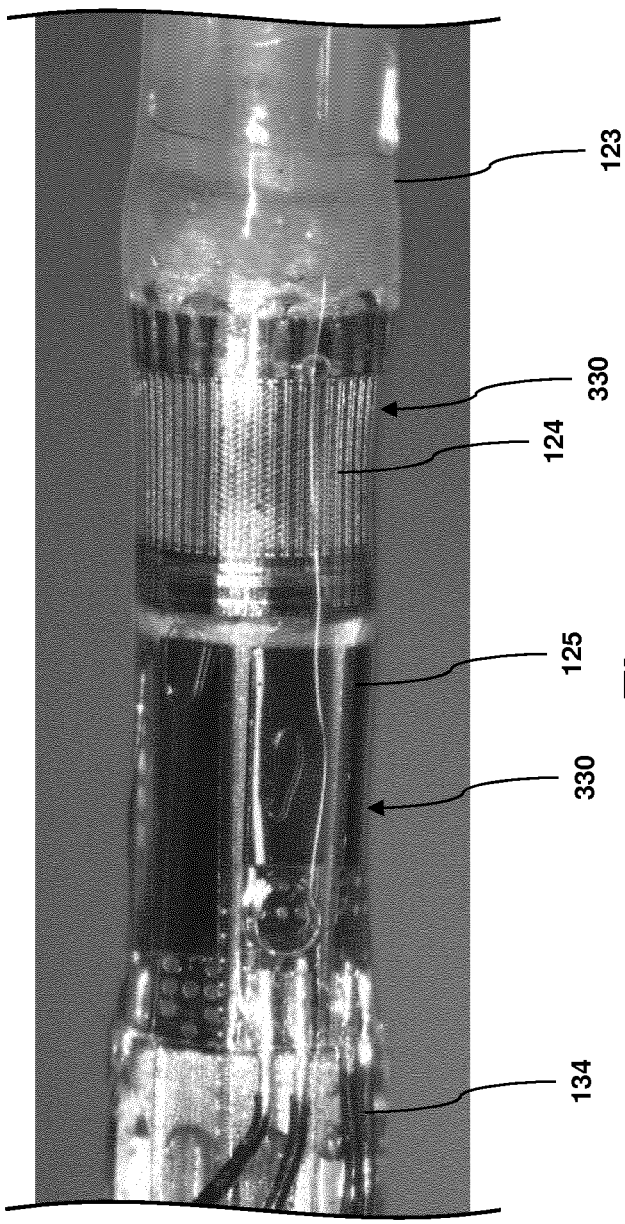

As a result of the steps of the method 400, the layer 330 is formed around the array 124, as shown in FIG. 15. In that regard, FIG. 15 is a diagrammatic top view after shrinking the tubing and curing the adhesive to form the acoustically-transparent window 300, according to an embodiment of the present disclosure. The adhesive layer 320 and flexible layer 310 are positioned between the array 124 and the layer 330 (FIG. 3). In some instances, the layer 330 can also cover the controllers 125.

In some embodiments, the acoustic window 300 has a thickness which varies across its extent. In these embodiments, the method of fabricating or assembling the intraluminal ultrasound imaging device may vary to that outlined above. In particular, one or more of steps 420 to 480 outlined above may vary.

One example approach for steps for fabricating the device with a varying thickness acoustic window is as follows. This approach is applicable in particular for an elongate member which has a round cross-section.

An imaging assembly comprising a plurality of acoustic elements is provided coupled to a distal portion of an elongate member.

The shape of the variable thickness acoustically-transparent window 300 may be controlled in the application process of the lowermost layer, e.g. PBR layer. This layer is applied to the assembled elongate member and imaging assembly arrangement.

The elongate member is rotated while the material of the lowermost layer is continuously deposited. The procedure will be described for an example material of PBR. However, this is for illustration only and the same approach can be used for other materials.

The amount of PBR applied is controlled by for instance measuring the diameter of a droplet on a syringe tip with a camera, or pumping the fluid to a tip of a needle for a predefined time. Then the droplet makes contact with the elongate member that is rotating. As a result of the rotation, a PBR ring or donut is formed around the imaging assembly. The height and width of the deposited PBR region is controlled by the surface tension (influenced by imaging assembly surface material and surface condition, e.g. whether or not the surface has been plasma cleaned, and the viscosity of the dissolved PBR solution).

The thickness (radial direction) of the layer is varied along the length direction of the elongate member, to thereby realize the thickness variation (e.g. wedge shape) of the window element along the length direction. For example, the thickness may be varied linearly along the length direction to achieve a window having thickness which increases linearly along its length direction.

The ring of PBR material is then dried. While drying, the ring shrinks by the same fraction at all points around its circumference. In this way a very well controlled PBR layer with thickness variation (along the length direction of the elongate member) may be deposited.

Figure 16:
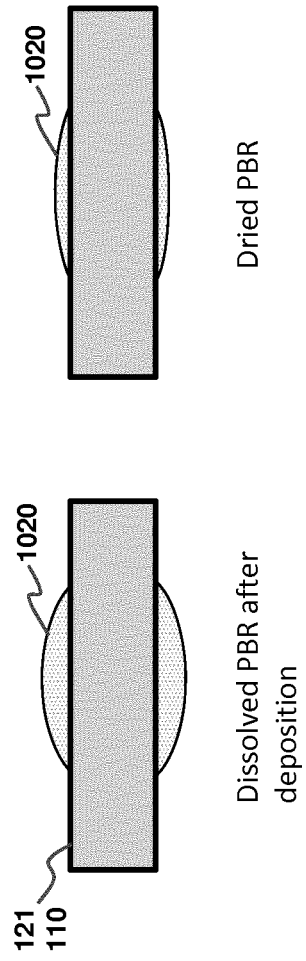

When approximately half of the ring (along the length direction) has been deposited on the elongate member and imaging assembly arrangement, effectively a wedge is formed above the acoustic elements of the imaging assembly. This is illustrated in FIG. 16 (left). The half-ring of deposited PBR 1020 is shown. Material outside the area of interest can be removed.

FIG. 16 (right) shows the deposited PBR 1020 after drying.

Following this step, the deposited PBR may be covered with a PET heat shrink (tubing), applied atop a PU adhesive layer. These materials represent only one example set of materials which may be used for forming the outermost layer and adhesive layer respectively, and other materials may alternatively be used, as outlined above for example.

The heat shrink (and thin PU adhesive layer) follow the shape of the deposited PBR. Different shapes may be formed by varying the shape of the deposited PBR innermost layer along the length direction (the elongate length of the elongate member). For example, a linearly sloping shape may be provided to the acoustic window. One ring may be deposited, or multiple rings may be deposited. Also concave shapes are possible.

By way of example, the example shape shown in FIGS. 8 and 9 above may be formed by depositing multiple rings. The window of FIG. 8 for example may be formed by depositing two adjacent rings, with appropriately sloping thickness in the length direction, and the arrangement of FIG. 9 formed by depositing six adjacent rings with appropriately sloping thickness in the length direction.

Alternatively, the example shapes shown in FIG. 8 or 9, may be formed by depositing an initial homogenous-height layer of PBR, and then, subsequent to drying of the layer, ablating the deposited layer in appropriate areas in such a way as to shape it to define the particular relief pattern required for these shapes. The PET layer may then be deposited atop this shaped PBR layer, which layer shrinks to follow the shaped topography of the PBR layer, as described above.

Figure 17:
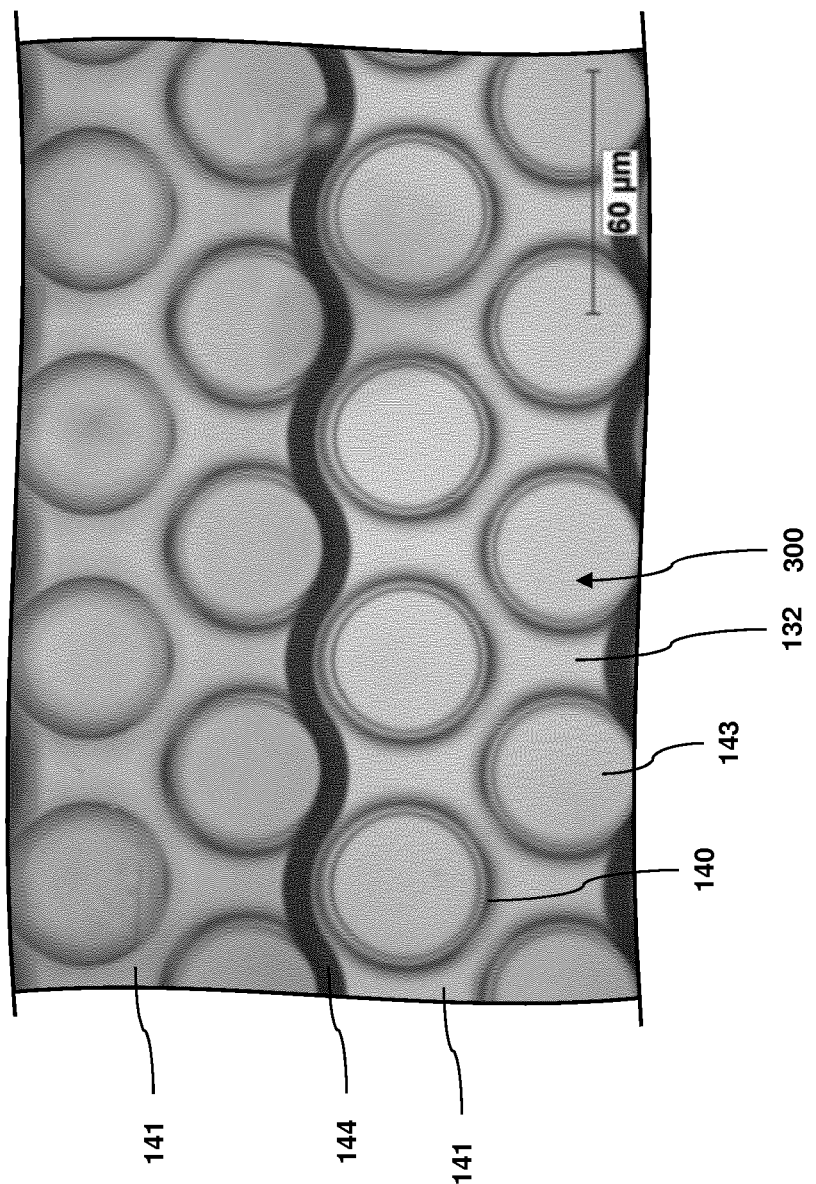

FIG. 17 is a diagrammatic top view of CMUT elements visible through the acoustically-transparent window, according to an embodiment of the present disclosure. FIG. 17 illustrates a portion of the array 124 after the steps of the method 400. The CMUT elements 140 are formed on islands 141 of the substrate 132 that are separated by the trench 144. The membrane 143 is visible through the optically and acoustically-transparent window 300A void free acoustically-transparent window 300 is advantageously realized according to aspects of the present disclosure.

Persons skilled in the art will recognize that the apparatus, systems, and methods described above can be modified in various ways. Accordingly, persons of ordinary skill in the art will appreciate that the embodiments encompassed by the present disclosure are not limited to the particular embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An intraluminal ultrasound imaging device, comprising:
   a flexible elongate member configured to be positioned within a body lumen of a patient, the flexible elongate member comprising a proximal portion, a distal portion, and a longitudinal axis; and
   an ultrasound imaging assembly disposed at the distal portion of the flexible elongate member and configured to obtain imaging data while positioned within the body lumen, the ultrasound imaging assembly comprising:
   a plurality of substrate islands;

a plurality of acoustic elements formed on each of the plurality of substrate islands, wherein the plurality of acoustic elements comprises a plurality of capacitive micromachined ultrasound transducer (CMUT) elements, wherein each of the plurality of CMUT elements comprises a membrane movable relative to the plurality of substrate islands;

a flexible interconnect coupled to the plurality of substrate islands such that the flexible interconnect directly contacts the membrane and the plurality of substrate islands is arranged around the longitudinal axis of the flexible elongate member, wherein the flexible interconnect comprises a plurality of openings, each opening of the plurality of openings overlapping with an associated acoustic element of the plurality of acoustic elements; and an acoustically-transparent window disposed over the plurality of acoustic elements, the acoustically-transparent window comprising a plurality of layers formed on top of one another, wherein the plurality of layers comprises:
an innermost layer directly contacting the membrane;
an outermost layer opposite the innermost layer; and
an adhesive layer coupling the outermost layer to another layer of the plurality of layers,
wherein the acoustically-transparent window is disposed over the flexible interconnect.

2. The intraluminal ultrasound imaging device of claim 1, wherein the flexible elongate member comprises a catheter.

3. The intraluminal ultrasound imaging device of claim 1, wherein the ultrasound imaging assembly comprises an intravascular ultrasound (IVUS) imaging assembly.

4. The intraluminal ultrasound imaging device of claim 1, wherein the innermost layer comprises an elastic material deformable upon movement of the membrane.

5. The intraluminal ultrasound imaging device of claim 1, wherein the innermost layer comprises polybutadiene rubber (PBR).

6. The intraluminal ultrasound imaging device of claim 1, wherein the outermost layer comprises polyethylene terephthalate (PET).

7. The intraluminal ultrasound imaging device of claim 1, wherein the adhesive layer comprises polyurethane (PU).

8. The intraluminal ultrasound imaging device of claim 1, wherein a thickness of the acoustically-transparent window varies across its extent.

9. The intraluminal ultrasound imaging device of claim 8, wherein the plurality of acoustic elements comprises an arrangement of one or more lines of elements, and wherein the thickness of the acoustically-transparent window varies along a direction of said one or more lines.

10. The intraluminal ultrasound imaging device of claim 8, wherein the thickness of the acoustically-transparent window varies along the direction of said longitudinal axis of the flexible elongate member.

11. The intraluminal ultrasound imaging device of claim 8, wherein the varying thickness of the acoustically-transparent window is such that the window has a wedge shape.

12. The intraluminal ultrasound imaging device of claim 1, wherein the thickness of the acoustically-transparent window varies smoothly across its extent, such that an uppermost surface of the window inclines or declines smoothly at one or more rates across the window.

13. The intraluminal ultrasound imaging device of claim 1, wherein the thickness of the acoustically-transparent window oscillates smoothly between a lower and upper thickness level, such that an uppermost surface of the window inclines and declines across the window between an lower and upper surface level.

14. The intraluminal ultrasound imaging device of claim 1,
wherein a hardness of the innermost layer is less than a hardness of every other layer of the plurality of layers, and
wherein a hardness of the outermost layer is greater than the hardness of every other layer of the plurality of layers.

15. The intraluminal ultrasound imaging device of claim 1, wherein the outermost layer comprises a tubing.

16. The intraluminal ultrasound imaging device of claim 15, wherein the tubing comprises a shrink wrap tubing.

17. The intraluminal ultrasound imaging device of claim 1, wherein the acoustic window directly contacts the flexible interconnect.

18. The intraluminal ultrasound imaging device of claim 1, wherein each opening of the plurality of openings is aligned with the associated acoustic element of the plurality of acoustic elements.

19. An intraluminal ultrasound imaging system, comprising:
an ultrasound imaging catheter configured to obtain imaging data while positioned within a body lumen of a patient, the ultrasound imaging catheter comprising a proximal portion, a distal portion, and a longitudinal axis, wherein the ultrasound imaging catheter further comprises:
a plurality of substrate islands;
a plurality of acoustic elements formed on each of the plurality of substrate islands, wherein the plurality of acoustic elements comprises a plurality of capacitive micromachined ultrasound transducer (CMUT) elements, wherein each of the plurality of CMUT elements comprises a membrane movable relative to the plurality of substrate islands;
a flexible interconnect coupled to the plurality of substrate islands such that the flexible interconnect directly contacts the membrane and the plurality of substrate islands is arranged around the longitudinal axis at the distal portion, wherein the flexible interconnect comprises a plurality of openings, each opening of the plurality of openings overlapping with an associated acoustic element of the plurality of acoustic elements; and
an acoustically-transparent window disposed over the plurality of acoustic elements, the acoustically-transparent window comprising:
a first material layer positioned over and directly contacting the membrane;
a second material layer positioned over and directly contacting the first material layer; and
a third material layer positioned over and directly contacting the second material layer,
wherein the second material layer couples the first material layer and the third material layer, and
wherein the acoustically-transparent window is disposed over the flexible interconnect; and
a processor in communication with the ultrasound imaging catheter and configured to output, to a display, an ultrasound image based on the obtained imaging data.

20. The intraluminal ultrasound imaging system of claim 19, wherein the ultrasound imaging catheter comprises an intravascular ultrasound (IVUS) catheter.

21. The intraluminal ultrasound imaging system of claim 19,
wherein the first material layer comprises an elastic material deformable upon movement of the membrane.

22. The intraluminal ultrasound imaging system of claim 19, wherein the first material layer comprises polybutadiene rubber (PBR).

23. The intraluminal ultrasound imaging system of claim 19, wherein the third material layer comprises polyethylene terephthalate (PET).

24. The intraluminal ultrasound imaging system of claim 19, wherein the second material layer comprises polyurethane (PU).

25. The intraluminal ultrasound imaging system of claim 19,
wherein the first material layer comprises a first hardness,
wherein the second material layer comprises a second hardness,
wherein the third material layer comprises a tubing having a third hardness,
wherein the first hardness is less than the second hardness and the third hardness, and
wherein the third hardness is greater than the first hardness and the second hardness.

26. The intraluminal ultrasound imaging system of claim 25, wherein the tubing comprises a shrink wrap tubing.

* * * * *